United States Patent
Nakamura et al.

(10) Patent No.: US 10,939,823 B2
(45) Date of Patent: Mar. 9, 2021

(54) IMAGE ANALYSIS DEVICE, IMAGE ANALYSIS METHOD, AND ILLUMINATION DEVICE

(71) Applicant: SONY CORPORATION, Tokyo (JP)

(72) Inventors: Kenichiro Nakamura, Saitama (JP); Takayuki Yamazaki, Aichi (JP); Kazuhito Kunishima, Aichi (JP)

(73) Assignee: SONY CORPORATION, Tokyo (JP)

( * ) Notice: Subject to any disclaimer, the term of this patent is extended or adjusted under 35 U.S.C. 154(b) by 1279 days.

(21) Appl. No.: 15/100,677

(22) PCT Filed: Dec. 5, 2014

(86) PCT No.: PCT/JP2014/082213
§ 371 (c)(1),
(2) Date: Jun. 1, 2016

(87) PCT Pub. No.: WO2015/093314
PCT Pub. Date: Jun. 25, 2015

(65) Prior Publication Data
US 2016/0296119 A1 Oct. 13, 2016

(30) Foreign Application Priority Data

Dec. 16, 2013 (JP) ............................. JP2013-258861
Jul. 18, 2014 (JP) ............................. JP2014-147300

(51) Int. Cl.
*A61B 5/00* (2006.01)
*G01N 21/21* (2006.01)
(Continued)

(52) U.S. Cl.
CPC .......... *A61B 5/0077* (2013.01); *A61B 5/0071* (2013.01); *A61B 5/0075* (2013.01);
(Continued)

(58) Field of Classification Search
CPC ... A61B 5/0071; A61B 5/0075; A61B 5/0077; A61B 5/443; A61B 5/742; A61B 5/7475;
(Continued)

(56) References Cited

U.S. PATENT DOCUMENTS

| 2006/0253175 | A1* | 11/2006 | Fan ........................ A61N 5/062 607/88 |
| 2008/0180950 | A1* | 7/2008 | Kang .................... A61B 5/0059 362/249.16 |
| 2013/0207136 | A1* | 8/2013 | Cheng ................. H01L 25/0753 257/89 |

FOREIGN PATENT DOCUMENTS

| JP | 11-163414 A | 6/1999 |
| JP | 2002-200050 A | 7/2002 |

(Continued)

OTHER PUBLICATIONS

Bae et al., "Multimodal facial color imaging modality for objective analysis of skin lesions", Journal of Biomedical Optics 13(6), pp. 0640071-064007-8 (Nov./Dec. 2008) (Year: 2008).*

*Primary Examiner* — Boniface N Nganga
(74) *Attorney, Agent, or Firm* — Chip Law Group

(57) ABSTRACT

Provided is an image analysis device, an image analysis method, and an illumination device to efficiently acquire an image to be suitably used to analyze skin. An image acquisition unit is included, the image acquisition unit including an illumination unit including a light emitting unit in which a plurality of light emitting elements including at least a light emitting element that emits visible light and a light emitting element that emits invisible light are packaged, and an image pickup unit that captures an image of reflection light generated by causing irradiation light emitted from the illumination unit to be reflected by an analysis target. The present disclosure is applicable to, for example, a device for analyzing human skin.

13 Claims, 33 Drawing Sheets

(51) Int. Cl.
*G01N 21/27* (2006.01)
*G01N 21/17* (2006.01)
*G06T 7/00* (2017.01)

(52) U.S. Cl.
CPC ............ *A61B 5/443* (2013.01); *G01N 21/21* (2013.01); *G01N 21/27* (2013.01); *G06T 7/0012* (2013.01); *A61B 5/742* (2013.01); *A61B 5/7475* (2013.01); *A61B 2576/00* (2013.01); *G01N 2021/1765* (2013.01); *G01N 2021/1772* (2013.01); *G01N 2201/062* (2013.01); *G01N 2201/12* (2013.01); *G06T 2207/10024* (2013.01); *G06T 2207/10048* (2013.01); *G06T 2207/30088* (2013.01)

(58) Field of Classification Search
CPC .... A61B 2576/00; G01N 21/21; G01N 21/27; G01N 2021/1765; G01N 2021/1772; G01N 2021/062; G01N 2021/12; G06T 7/0012; G06T 2207/10024; G06T 2207/10048; G06T 2207/30088
See application file for complete search history.

(56) References Cited

FOREIGN PATENT DOCUMENTS

| | | | |
|---|---|---|---|
| JP | 2003-333608 A | 11/2003 | |
| JP | 2005-006725 A | 1/2005 | |
| JP | 2009-000494 A | 1/2009 | |
| JP | 4521587 B | 8/2010 | |
| JP | 2013-212247 A | 10/2013 | |
| WO | 2005/071372 A1 | 8/2005 | |
| WO | WO-2013084919 A1 * | 6/2013 | ............... F21V 5/04 |
| WO | WO-2013160780 A1 * | 10/2013 | ........... A61B 1/0638 |
| WO | WO-2014007869 A9 * | 2/2014 | ............... G01J 3/36 |

* cited by examiner

FIG. 9

| MEASUREMENT ITEM | COLOR OF SKIN | SHINE | PORE | TEXTURE | INTERNAL MELANIN INDEX | SURFACE MELANIN INDEX | INTERNAL ERYTHEMA INDEX | SURFACE ERYTHEMA INDEX |
|---|---|---|---|---|---|---|---|---|
| IRp | | | | | | O | | |
| Bp | O | O | | | | | | |
| Gp | O | O | | O | | | | O |
| Rp | O | O | | | | O | O | |
| IRr | | | | | O | | | |
| Br | O | | | | | | | |
| Gr | O | | O | | | | O | |
| Rr | O | | | O | O | | | |

FIG. 11

| MEASUREMENT ITEM | Rr | Gr | Br | UVr | Rp | Gp | Bp | UVp |
|---|---|---|---|---|---|---|---|---|
| COLOR OF SKIN | ○ | ○ | ○ | | ○ | ○ | ○ | |
| SHINE | | | | | ○ | ○ | ○ | |
| PORE | | ○ | | | | | | |
| TEXTURE | ○ | | | | | ○ | | |
| INTERNAL ERYTHEMA INDEX | | ○ | | | | | | |
| SURFACE ERYTHEMA INDEX | | | | | ○ | | | |
| PORPHYRIN | | | | ○ | | ○ | | ○ |

FIG. 13

| MEASUREMENT ITEM | Rr | Gr | Br | IRr | Rp | Gp | Bp | UVp |
|---|---|---|---|---|---|---|---|---|
| COLOR OF SKIN | ○ | ○ | ○ | | ○ | ○ | ○ | |
| SHINE | | | | | ○ | ○ | ○ | |
| PORE | | ○ | | | | | | |
| TEXTURE | | | | | | ○ | | |
| INTERNAL MELANIN INDEX | ○ | | | ○ | | | | |
| INTERNAL ERYTHEMA INDEX | ○ | ○ | | | | | | |
| SURFACE ERYTHEMA INDEX | | | | | ○ | ○ | | |
| PORPHYRIN | | | | | | | | ○ |

FIG.15

| Rr | Gr | Br | IRr | R | G | B | UV | MEASUREMENT ITEM |
|---|---|---|---|---|---|---|---|---|
| ○ | ○ | ○ |  | ○ | ○ | ○ |  | COLOR OF SKIN |
|  |  |  |  | ○ | ○ | ○ |  | SHINE |
|  | ○ |  |  |  |  |  |  | PORE |
| ○ |  |  |  |  | ○ |  |  | TEXTURE |
|  |  |  | ○ |  |  |  |  | INTERNAL MELANIN INDEX |
|  |  |  |  | ○ |  |  |  | ERYTHEMA INDEX |
|  |  |  |  |  |  |  | ○ | PORPHYRIN |

FIG.17

| MEASUREMENT ITEM | COLOR OF SKIN | SHINE | PORE | TEXTURE | INTERNAL MELANIN INDEX | SURFACE MELANIN INDEX | INTERNAL ERYTHEMA INDEX | SURFACE ERYTHEMA INDEX | PORPHYRIN |
|---|---|---|---|---|---|---|---|---|---|
| UVp | | | | | | | | | ○ |
| IRp | | | | | | ○ | | | |
| Bp | ○ | ○ | | | | | | | |
| Gp | ○ | ○ | | ○ | | | | ○ | |
| Rp | ○ | ○ | | | | ○ | | ○ | |
| UVr | | | | | | | | | ○ |
| IRr | | | | ○ | | | | | |
| Br | ○ | | | | | | | | |
| Gr | ○ | | ○ | | | | ○ | | |
| Rr | ○ | | | ○ | | | ○ | | |

FIG. 19

| MEASUREMENT ITEM | Rr | Gr | IRr | UVr | Wr | Rp | Gp | IRp | UVp | Wp |
|---|---|---|---|---|---|---|---|---|---|---|
| COLOR OF SKIN | | | | | ○ | | | | | ○ |
| SHINE | | ○ | | | | | | | | ○ |
| PORE | | | | | | | | | | |
| TEXTURE | | | ○ | | | | ○ | | | |
| INTERNAL MELANIN INDEX | ○ | | | | | | | | | |
| SURFACE MELANIN INDEX | | | | | | ○ | | ○ | | |
| INTERNAL ERYTHEMA INDEX | ○ | ○ | | | | | | | | |
| SURFACE ERYTHEMA INDEX | | | | | | ○ | ○ | | | |
| PORPHYRIN | | | | ○ | | | | | ○ | |

FIG. 21

| R | G | IR | Wr | UV | W | MEASUREMENT ITEM |
|---|---|----|----|----|---|------------------|
|   |   |    | ○  |    | ○ | COLOR OF SKIN    |
|   |   |    | ○  |    |   | PORE             |
|   |   |    |    |    | ○ | TEXTURE          |
| ○ |   |    |    |    |   | MELANIN INDEX    |
|   |   | ○  |    |    |   |                  |
| ○ |   |    |    |    |   | ERYTHEMA INDEX   |
|   | ○ |    |    |    |   |                  |
|   |   |    |    | ○  |   | PORPHYRIN        |

FIG. 24

| MEASUREMENT ITEM | COLOR OF SKIN | SHINE | PORE | TEXTURE | INTERNAL MELANIN INDEX | SURFACE MELANIN INDEX | INTERNAL ERYTHEMA INDEX | SURFACE ERYTHEMA INDEX | PORPHYRIN |
|---|---|---|---|---|---|---|---|---|---|
| UV |  |  |  |  |  |  |  |  | O |
| IRp |  |  |  |  |  |  |  |  |  |
| IRp |  |  |  |  |  | O |  |  |  |
| Bp |  | O |  |  |  |  |  |  |  |
| Gp |  | O |  |  |  |  |  | O |  |
| Rp |  | O |  |  |  | O |  | O |  |
| IRr |  |  |  |  | O |  |  |  |  |
| Br |  |  |  |  |  |  |  |  |  |
| Gr |  |  |  |  |  |  | O |  |  |
| Rr |  |  |  |  | O |  | O |  |  |
| Wr | O |  | O |  |  |  |  |  |  |
| W | O |  |  | O |  |  |  |  |  |

IMAGE ANALYSIS DEVICE, IMAGE ANALYSIS METHOD, AND ILLUMINATION DEVICE

CROSS REFERENCE TO RELATED APPLICATIONS

This application is a U.S. National Phase of International Patent Application No. PCT/JP2014/082213 filed on Dec. 5, 2014, which claims priority benefit of Japanese Patent Application No. JP 2013-258861 filed in the Japan Patent Office on Dec. 16, 2013 and JP 2014-147300 filed in the Japan Patent Office on Jul. 18, 2014. Each of the above-referenced applications is hereby incorporated herein by reference in its entirety.

TECHNICAL FIELD

The present disclosure relates to an image analysis device, an image analysis method, a program, and an illumination device and particularly relates to an image analysis device, an image analysis method, a program, and an illumination device which are suitably used to analyze, for example, a state of human skin.

BACKGROUND ART

Conventionally, there has been a skin image acquisition device that captures an image for analyzing a state of human skin. The skin image acquisition device includes an illumination unit including a light source such as an LED and a camera including a lens and an image pickup element and is configured so that the camera captures an image in a state in which skin is irradiated with light from the illumination unit.

For example, Patent Literature 1 discloses an invention in which an image is captured by using a white LED and a UV LED for illumination and the image obtained as a result is analyzed.

CITATION LIST

Patent Literature

Patent Literature 1: JP 2005-6725A

SUMMARY OF INVENTION

Technical Problem

In the case where a white LED and a UV LED are used for illumination as described above, irradiation light is specularly reflected in a part of skin, and this causes uneven illuminance, that is, an image of this part is captured as so-called shine. Thus, an image to be suitably used to analyze skin cannot be obtained in some cases.

In the conventional skin image acquisition device, light sources included in the illumination unit have only a few types of wavelengths, and therefore analyzable items are limited. As a countermeasure for this, it is considered that a plurality of LEDs for generating light having different wavelengths, respectively, are simply provided in the illumination unit. However, in that case, a size of the illumination unit is increased, and therefore the skin image acquisition device cannot be easily used by a user.

The present disclosure has been made in view of the circumstances and is to efficiently acquire an image to be suitably used to analyze skin.

Solution to Problem

An image analysis device according to a first aspect of the present disclosure includes an image acquisition unit including an illumination unit including a light emitting unit in which a plurality of light emitting elements including at least a light emitting element configured to emit visible light and a light emitting element configured to emit invisible light are packaged, and an image pickup unit configured to capture an image of reflection light generated by causing irradiation light emitted from the illumination unit to be reflected by an analysis target.

In the light emitting unit, the plurality of light emitting elements including at least a light emitting element configured to emit red light that is visible light, a light emitting element configured to emit green light that is visible light, and a light emitting element configured to emit infrared radiation that is invisible light may be packaged.

The image acquisition unit may further include a polarizer arranged in an optical path of the irradiation light emitted from the illumination unit, and an analyzer arranged in an optical path in which the reflection light is incident on the image pickup unit.

The image acquisition unit may further include a light guide member configured to guide the irradiation light emitted from the irradiation unit to the analysis target.

The light guide member may have an arbitrary optical surface shape.

The illumination unit may include the plurality of light emitting units. The plurality of light emitting units may be arranged at equal intervals around an optical axis of the image pickup unit.

The plurality of light emitting units forming the illumination unit may be planarly arranged at equal intervals around the optical axis of the image pickup unit.

The plurality of light emitting units forming the illumination unit may be three-dimensionally arranged at equal intervals around the optical axis of the image pickup unit so as to form a multilayer.

The plurality of light emitting units forming the illumination unit may be arranged at different angles so as to face the analysis target.

The illumination unit may change a wavelength of the irradiation light by changing the light emitting element to emit light in accordance with an analysis item.

The image analysis device according to the first aspect of the present disclosure may further include an operation input unit to which user operation for selecting the analysis item is input.

The image analysis device according to the first aspect of the present disclosure may further include an image analysis unit configured to analyze an image captured by the image pickup unit.

According to the first aspect of the present disclosure, an image analysis method uses an image analysis device that includes an image acquisition unit including an illumination unit including a light emitting unit in which a plurality of light emitting elements including at least a light emitting element configured to emit visible light and a light emitting element configured to emit invisible light are packaged, and an image pickup unit configured to capture an image of reflection light generated by causing irradiation light emitted from the illumination unit to be reflected by an analysis target, the method including: an irradiation step of emitting irradiation light by using the illumination unit; and an image capturing step of capturing, by using the image pickup unit, an image of reflection light generated by causing the irradiation light emitted from the illumination unit to be reflected by the analysis target.

According to the first aspect of the present disclosure, a program for controlling an image analysis device includes an image acquisition unit including an illumination unit including a light emitting unit in which a plurality of light emitting elements including at least a light emitting element configured to emit visible light and a light emitting element configured to emit invisible light are packaged, and an image pickup unit configured to capture an image of reflection light generated by causing irradiation light emitted from the illumination unit to be reflected by an analysis target, the program causing a computer of the image analysis device to execute processing including an illumination step of controlling the illumination unit in a manner that the illumination unit emits irradiation light, and an image capturing step of controlling the image pickup unit in a manner that the image pickup unit captures an image of reflection light generated by causing the irradiation light emitted from the illumination unit to be reflected by the analysis target.

According to the first aspect of the present disclosure, irradiation light is emitted by an illumination unit including a light emitting unit in which a plurality of light emitting elements including at least a light emitting element configured to emit visible light and a light emitting element configured to emit invisible light are packaged, and an image of reflection light generated by causing the emitted irradiation light to be reflected by an analysis target is captured.

An illumination device according to a second aspect of the present disclosure includes a plurality of light emitting units in which a plurality of light emitting elements including at least a light emitting element configured to emit visible light and a light emitting element configured to emit invisible light are packaged.

In the second aspect of the present disclosure, irradiation light is emitted by a plurality of light emitting units in which a plurality of light emitting elements including at least a light emitting element configured to emit visible light and a light emitting element configured to emit invisible light are packaged.

Advantageous Effects of Invention

According to the first aspect of the present disclosure, it is possible to efficiently acquire an image to be suitably used to analyze skin.

According to the second aspect of the present disclosure, it is possible to emit irradiation light for efficiently capturing an image to be suitably used to analyze skin.

BRIEF DESCRIPTION OF DRAWINGS

FIG. 9 shows correspondence between measurement items and ON of the light sources in the first arrangement example.

FIG. 11 shows correspondence between measurement items and ON of the light sources in the second arrangement example.

FIG. 13 shows correspondence between measurement items and ON of the light sources in the third arrangement example.

FIG. 15 shows correspondence between measurement items and ON of the light sources in the fourth arrangement example.

FIG. 17 shows correspondence between measurement items and ON of the light sources in the fifth arrangement example.

FIG. 19 shows correspondence between measurement items and ON of the light sources in the sixth arrangement example.

FIG. 21 shows correspondence between measurement items and ON of the light sources in the seventh arrangement example.

FIG. 24 shows correspondence between measurement items and ON of the light sources in the eighth arrangement example.

DESCRIPTION OF EMBODIMENTS

Hereinafter, best modes for carrying out the present disclosure (hereinafter, referred to as "embodiments") will be described. However, before that, characteristics of irradiation light also used in a skin analysis device according to this embodiment will be described.

Figure 1:
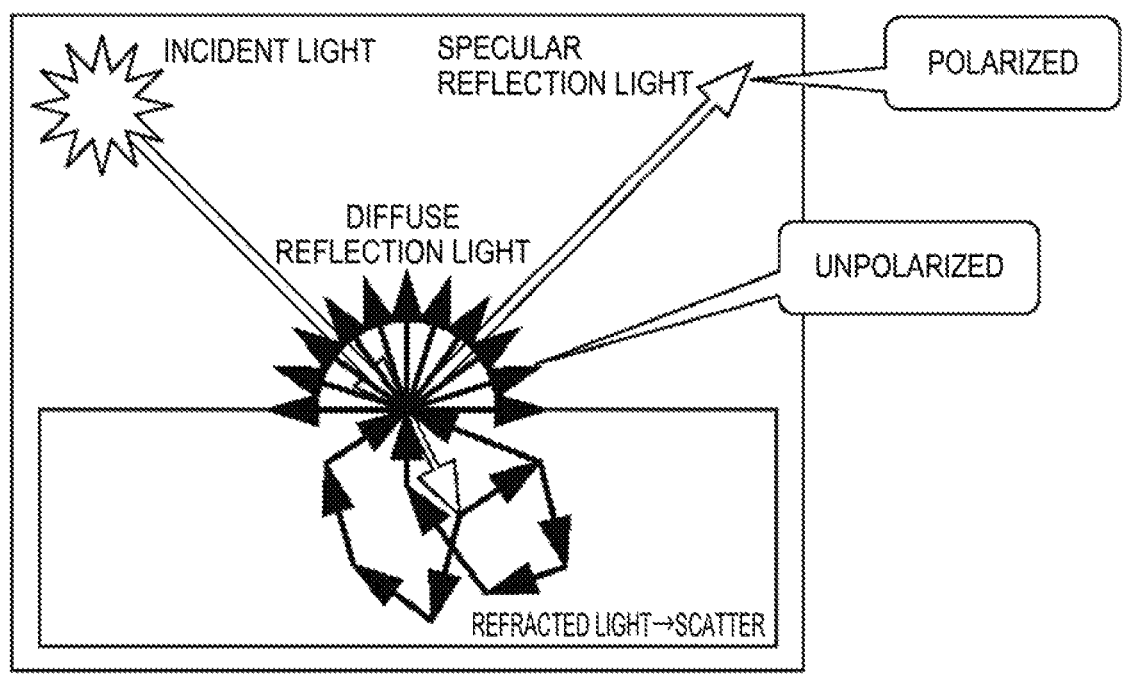
FIG. 1 illustrates a state in which light emitted from a light source is reflected by an analysis target.

FIG. 1 illustrates a state in which light emitted from a light source is reflected by an analysis target (skin in this embodiment).

As illustrated in FIG. 1, light, which is obtained by irradiating the analysis target with illumination light from the light source to cause the illumination light to be reflected by the analysis target, is classified into two categories: specular reflection light; and diffuse reflection light. The specular reflection light is light reflected at the same angle as an angle of incidence of irradiation light, and, in the case where the irradiation light is polarized, the irradiation light is reflected while a polarized state thereof is being kept. Meanwhile, the diffuse reflection light is light reflected in various directions regardless of an angle of incidence of irradiation light, and, in the case where the irradiation light is polarized, the irradiation light is reflected while a polarization state thereof is not being kept.

Figure 2:
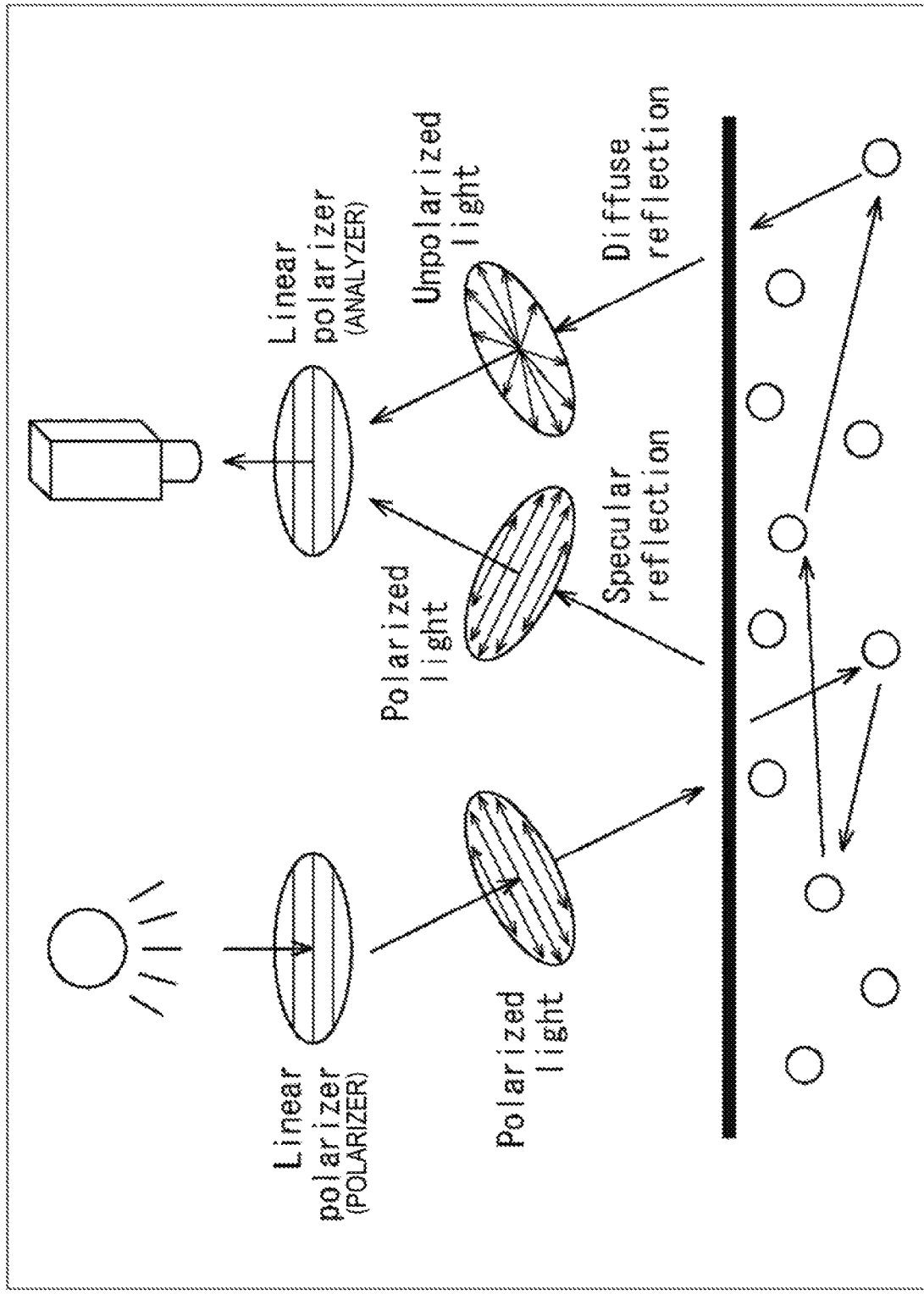
FIG. 2 illustrates a state in which polarizing plates are provided in respective optical paths of irradiation light and reflection light.

FIG. 2 illustrates a state in which a polarizing plate (hereinafter, referred to as "polarizer") is provided in front of a light source (in an optical path of irradiation light) and a polarizing plate (hereinafter, referred to as "analyzer") is provided in front of a camera for capturing an image of an analysis target (in an optical path of reflection light). In this case, the analysis target is irradiated with irradiation light from the light source in a polarization state based on the polarizer, and the polarization state caused by the polarizer is kept in specular reflection light thereof. Therefore, a light amount of specular reflection light to be incident on the camera can be controlled by adjusting a polarization direction of the polarizer or the analyzer.

Specifically, in the case where the polarization directions of the polarizer and the analyzer are in parallel to each other, specular reflection light can be transmitted through the analyzer to reach the camera. Meanwhile, in the case where the polarization directions of the polarizer and the analyzer are orthogonal to each other, specular reflection light is blocked by the analyzer, and therefore the specular reflection light does not reach the camera.

Therefore, a first light source in which a polarizer whose polarization direction is in parallel to that of the analyzer in front of the camera is provided in an optical path and a second light source in which a polarizer whose polarization direction is orthogonal to that of the analyzer in front of the camera is provided in an optical path are provided, and, in the case where light is emitted by switching the first light source and the second light source, the following two modes can be switched: a mode in which an image of a specular reflection light component is captured as it is; and a mode in which only an image of a diffuse reflection light component is captured while a specular reflection light component is being blocked.

Recognition of a substance based on a wavelength of illumination light will be described.

It is known that a substance generally has an inherent light absorption spectrum. There has been established spectroscopy in which a substance is recognized by irradiating an unknown sample with light whose wavelength is continuously changed, measuring a reflection light intensity thereof, and comparing the reflection light intensity with known spectra.

Note that, in the case where what substance is contained in a sample can be estimated, it is unnecessary to perform spectral measurement in a wide range of wavelengths, and presence/absence of the substance or a content rate thereof can be checked by selecting some wavelengths that may cause the substance to show a characteristic light absorption spectrum shape and irradiating the substance with light having those wavelengths.

Figure 3:
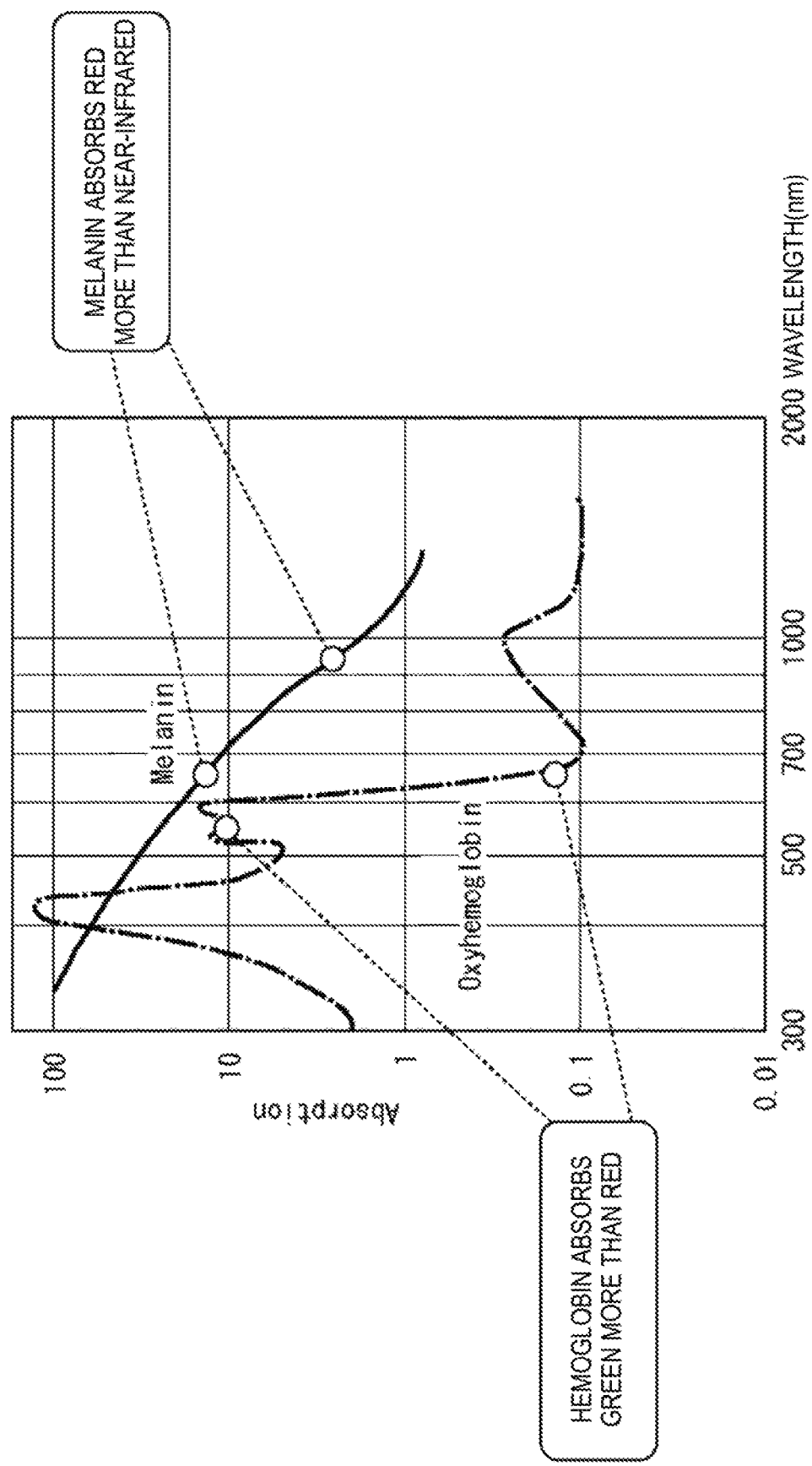
FIG. 3 shows light absorption spectra of hemoglobin and melanin.

FIG. 3 shows light absorption spectra of hemoglobin and melanin. As illustrated in FIG. 3, hemoglobin has a property that absorbs green light having wavelengths around 550 nm more than red light having wavelengths around 650 nm. In view of this, when a reflection light intensity is measured by using illumination light having those two ranges of wavelengths, reduction in reflection of green light is relatively larger than reduction in reflection of red light in a substance containing a large amount of hemoglobin. By using this property, presence/absence of hemoglobin and an amount thereof can be measured. Also in the case of a melanin pigment, similar measurement can be performed by using near-infrared light having wavelengths around 950 nm and red light having wavelengths around 650 nm.

Note that measurement of hemoglobin is used for measurement of erythematodes (hereinafter, abbreviated as "erythema") described below.

Recognizing a substance by using fluorescence excited by UV light serving as irradiation light will be described. A phenomenon in which energy applied to a substance, such as light and heat, is emitted from the substance as light is referred to as "luminescence", and the light emitted at that time is referred to as "fluorescence". A substance in which luminescence occurs is referred to as "fluorescent substance".

Emitted light in luminescence (photoluminescence) caused by applying light energy is ultraviolet rays or X-rays outside a visible light range in many cases. Note that UV light and X-rays are invisible with the naked eye, and an image thereof cannot be captured by a general camera. However, in the case where a wavelength of fluorescence excited by UV light or X-rays is in the visible light range, it is possible to measure presence/absence of fluorescent substances and an amount thereof by observing the fluorescence with the naked eye or capturing an image thereof by using a camera.

Note that measurement of fluorescent substances is used for measurement of porphyrin (waste matter of *Propionibacterium acnes* that cause pimples) described below.

Example Configuration of Skin Analysis Device According to Embodiment

Figure 4:
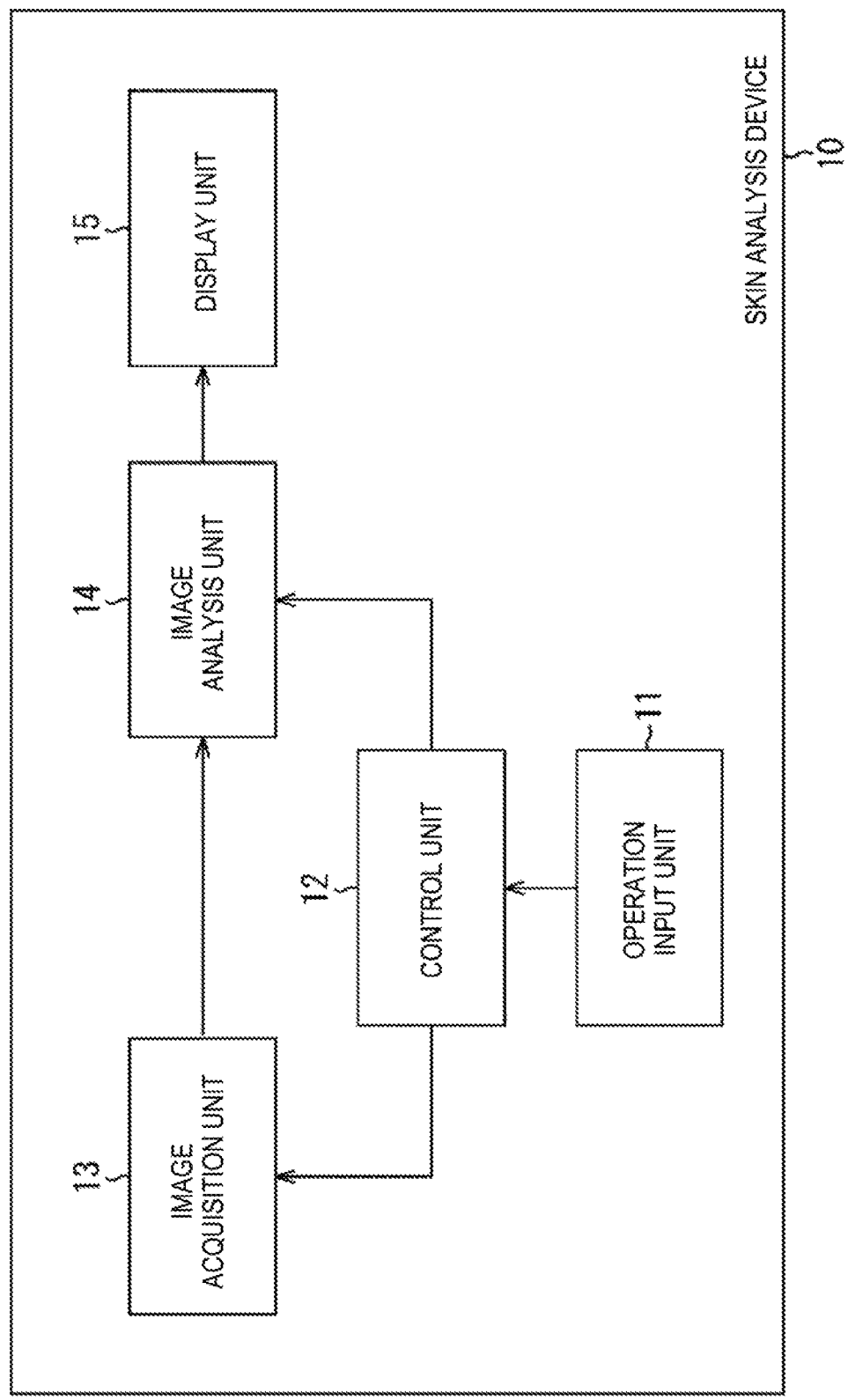
FIG. 4 is a block diagram showing an example configuration of a skin analysis device to which the present disclosure is applied.

FIG. 4 shows an example configuration of a skin analysis device according to an embodiment of the present disclosure.

This skin analysis device 10 includes an operation input unit 11, a control unit 12, an image acquisition unit 13, an image analysis unit 14, and a display unit 15.

The operation input unit 11 accepts user operation for selecting, for example, measurement items related to skin (for example, color, shine, pores, texture, a melanin index, an erythema index, and porphyrin of skin) and outputs an operation signal thereof to the control unit 12. The control unit 12 controls the image acquisition unit 13 and the image analysis unit 14 on the basis of the operation signal from the operation input unit 11.

The image acquisition unit 13 includes at least a light source that irradiates an analysis target (skin in this embodiment) with irradiation light and a camera that captures an image of the analysis target irradiated with irradiation light and outputs, to the image analysis unit 14, an image obtained by capturing an image of the analysis target. The image analysis unit 14 analyzes the image input from the image acquisition unit 13 to thereby measure the measurement items related to skin and outputs a measurement result to the display unit 15. The display unit 15 displays the measurement result output by the image analysis unit 14. Note that image analysis may be performed by using so-called cloud computing instead of providing the image analysis unit 14. Further, the measurement result may not only be displayed on the display unit 15 but also be displayed on another device (personal computer, smartphone, or the like) which is connectable to a network.

Operation of Skin Analysis Device

In the skin analysis device 10, an analysis target is irradiated with irradiation light and an image thereof is captured by the image acquisition unit 13 in accordance with a measurement item selected by a user, and the image obtained as a result is captured by the image analysis unit 14, and then an analysis result is displayed on the display unit 15.

Example Configuration of Image Acquisition Unit 13

A detailed example configuration of the image acquisition unit 13 will be described.

First Example Configuration of Image Acquisition Unit 13

Figure 5:
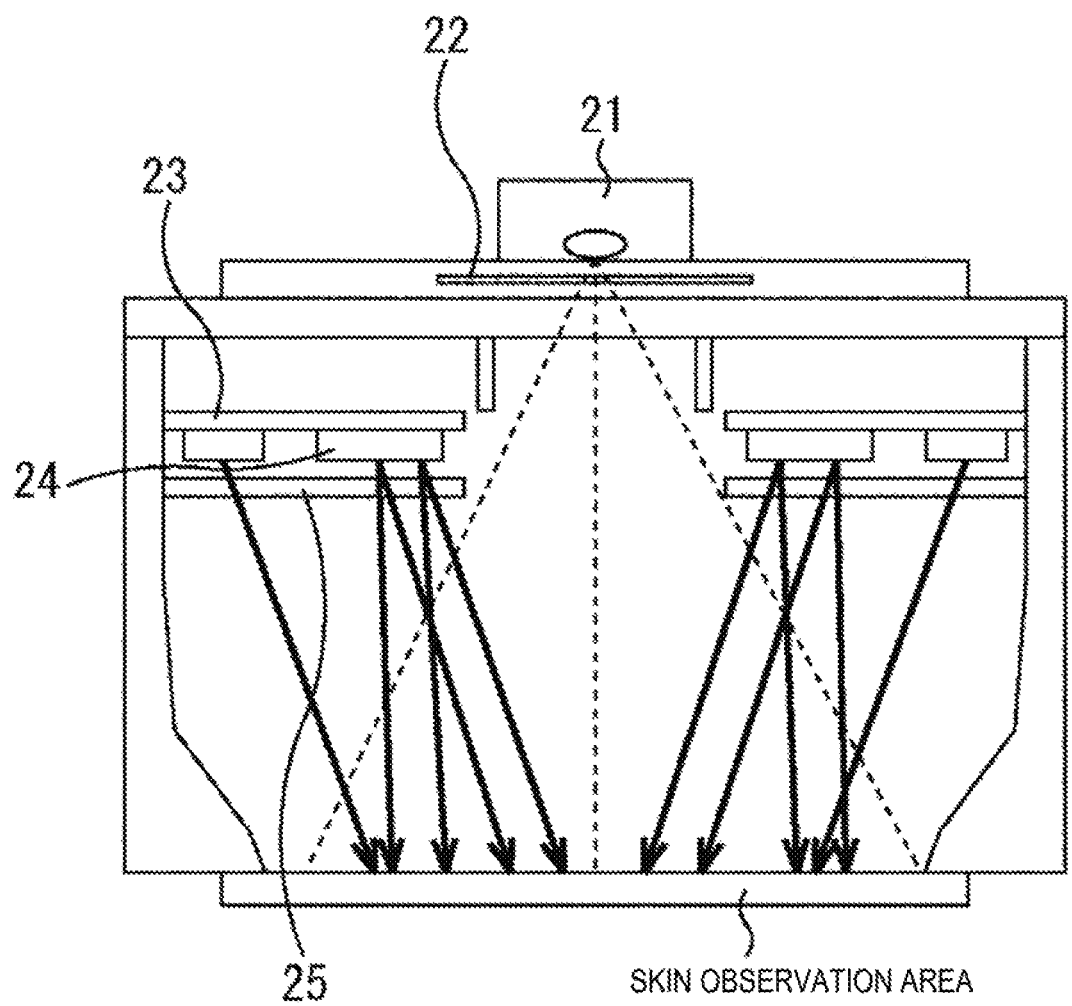
FIG. 5 is a cross-sectional view illustrating a first example configuration of an image acquisition unit in FIG. 4.

FIG. 5 illustrates a cross-section of a first example configuration of the image acquisition unit 13. The first example configuration fixes a camera 21 that captures an image of an analysis target, an analyzer 22 including a polarizing plate, and an illumination unit 24 and includes a printed circuit board (PCB) 23 including, for example, flexible printed circuits (FPCs) to be controlled, the illumination unit 24 including a plurality of light sources (LEDs), and a polarizer 25 constituted by a polarizing plate.

As illustrated in FIG. 5, an irradiation direction of the illumination unit 24 is set to be a direction facing the analysis target, and the polarizer 25 is arranged in front of the illumination unit 24 (in an optical path of irradiation light). Therefore, the analysis target is irradiated with irradiation light emitted from the illumination unit 24 via the polarizer 25.

Meanwhile, the analyzer 22 is arranged in front of the camera 21 (in an optical path of reflection light from the analysis target). Therefore, reflection light from the analysis target is incident on the camera 21 via the analyzer 22.

Note that polarization directions of the analyzer 22 and the polarizers 25 and light sources forming the illumination unit 24 will be described below.

Second Example Configuration of Image Acquisition Unit 13

Figure 6:
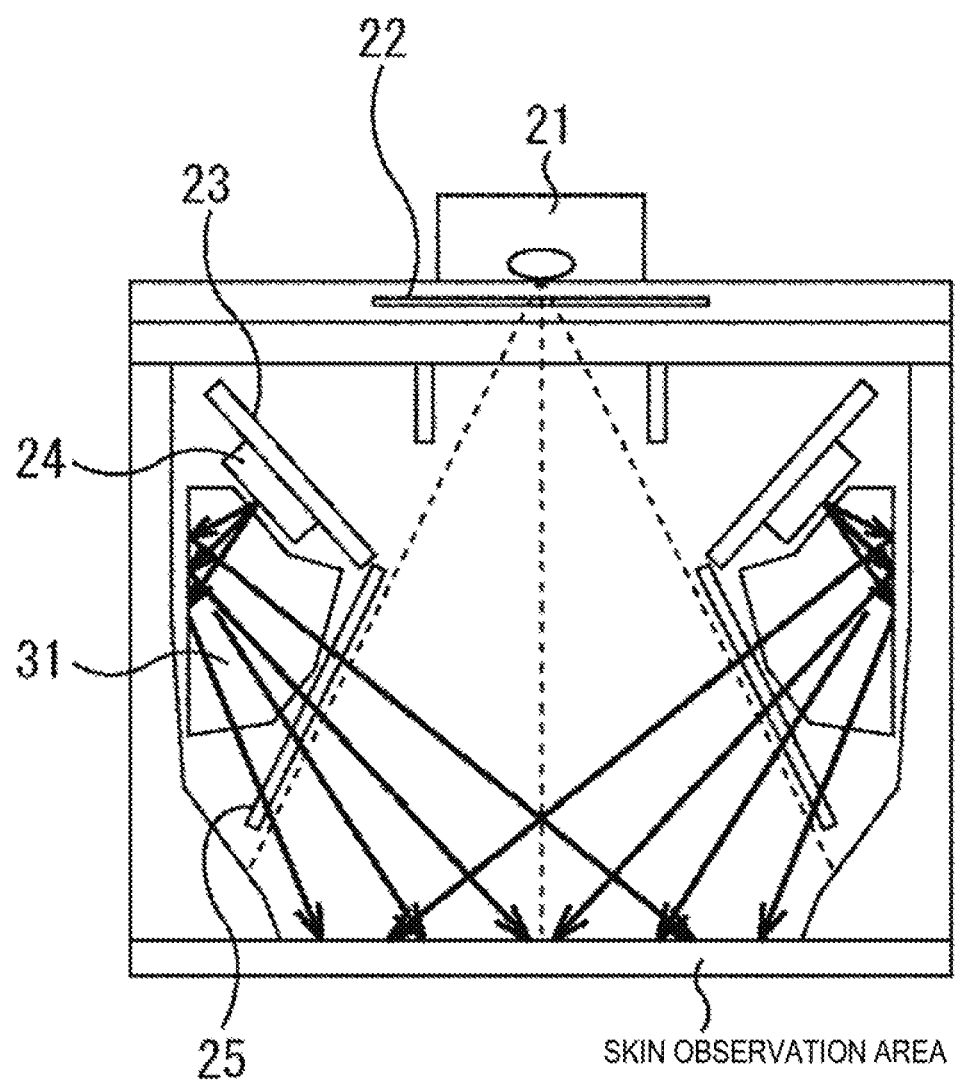
FIG. 6 is a cross-sectional view illustrating a second example configuration of an image acquisition unit in FIG. 4.

FIG. 6 illustrates a cross-section of a second example configuration of the image acquisition unit 13. The second example configuration includes the camera 21, the analyzer 22, the PCBs 23, the illumination unit 24, the polarizers 25, and light guide members 31. Note that constituent elements common to the first example configuration are denoted by the same numbers, and therefore description thereof is omitted.

The light guide member 31 is made of, for example, an optical member such as a lens, a light pipe, or an optical fiber and changes a travelling direction of irradiation light emitted by the illumination unit 24 to irradiate a skin observation area. Note that a central axis of (the light sources included in) the illumination unit 24 and a central axis of the light guide member 31 do not necessarily correspond to each other. Instead, irradiation light in an oblique direction can be emitted more efficiently by decentering both the central axes.

In the case of the second example configuration, an irradiation direction of the illumination unit 24 does not face an analysis target but is arranged to face a side surface of a housing. Further, the light guide member 31 and the polarizer 25 are arranged in front of the illumination unit 24. With this, an entire size of the image acquisition unit 13 of the second example configuration can be reduced, as compared with the first example configuration. In addition, the irradiation direction of the illumination unit 24 does not face a lower part of the housing, and therefore it is possible to suppress dazzle when the image acquisition unit 13 is seen from the lower part of the housing. The analysis target is irradiated with irradiation light emitted from the illumination unit 24 via the light guide member 31 and the polarizer 25.

Third Example Configuration of Image Acquisition Unit 13

Figure 7:
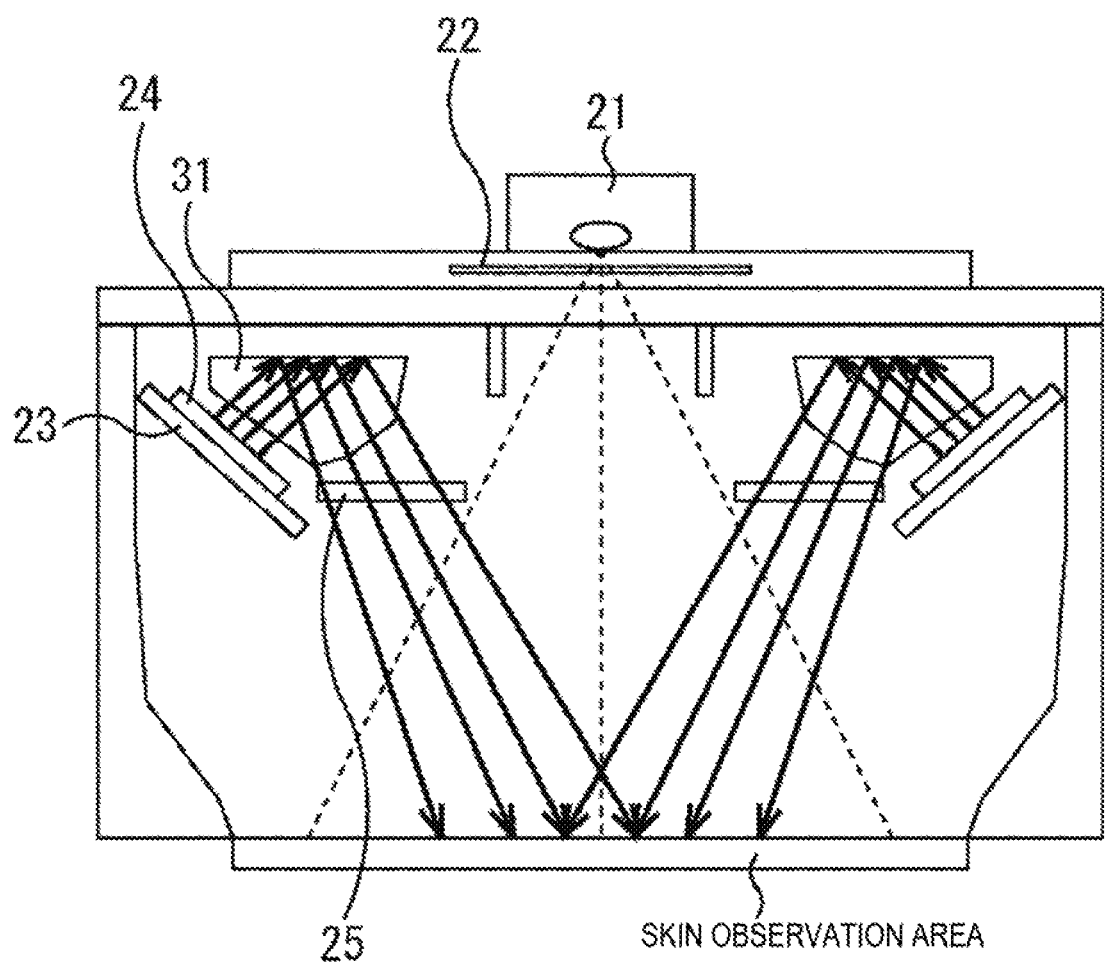
FIG. 7 is a cross-sectional view illustrating a third example configuration of an image acquisition unit in FIG. 4.

FIG. 7 illustrates a cross-section of a third example configuration of the image acquisition unit 13. The third example configuration, as well as the second configuration, includes the camera 21, the analyzer 22, the PCBs 23, the illumination unit 24, the polarizers 25, and the light guide members 31. Note that constituent elements common to the first example configuration are denoted by the same numbers, and therefore description thereof is omitted.

In the case of the third example configuration, an irradiation direction of the illumination unit 24 does not face an analysis target and is arranged to face an upper surface of the housing. The light guide member 31 and the polarizer 25 are arranged in front of the illumination unit 24. With this, the entire size of the image acquisition unit 13 of the third example configuration can be also reduced, as compared with the first example configuration. In addition, the irradiation direction of the illumination unit 24 does not face the lower part of the housing, and therefore it is possible to suppress dazzle when the image acquisition unit 13 is seen from the lower part of the housing. The analysis target is irradiated with irradiation light emitted from the illumination unit 24 via the light guide member 31 and the polarizer 25.

Note that a shape of an optical surface of the light guide member 31 is not limited to the illustrated shape. The optical surface has an arbitrary shape such as a curved surface, an aspherical surface, or a free form surface.

Light Sources Forming Illumination Unit 24

Light sources forming the planar illumination unit 24 will be described. Note that, hereinafter, first to seventh example configurations of the light sources forming the planar illumination unit 24 will be described, and those example configurations can be combined with any of the above first to third example configurations of the image acquisition unit 13.

First Arrangement Example of Light Sources Forming Illumination Unit 24

Figure 8:
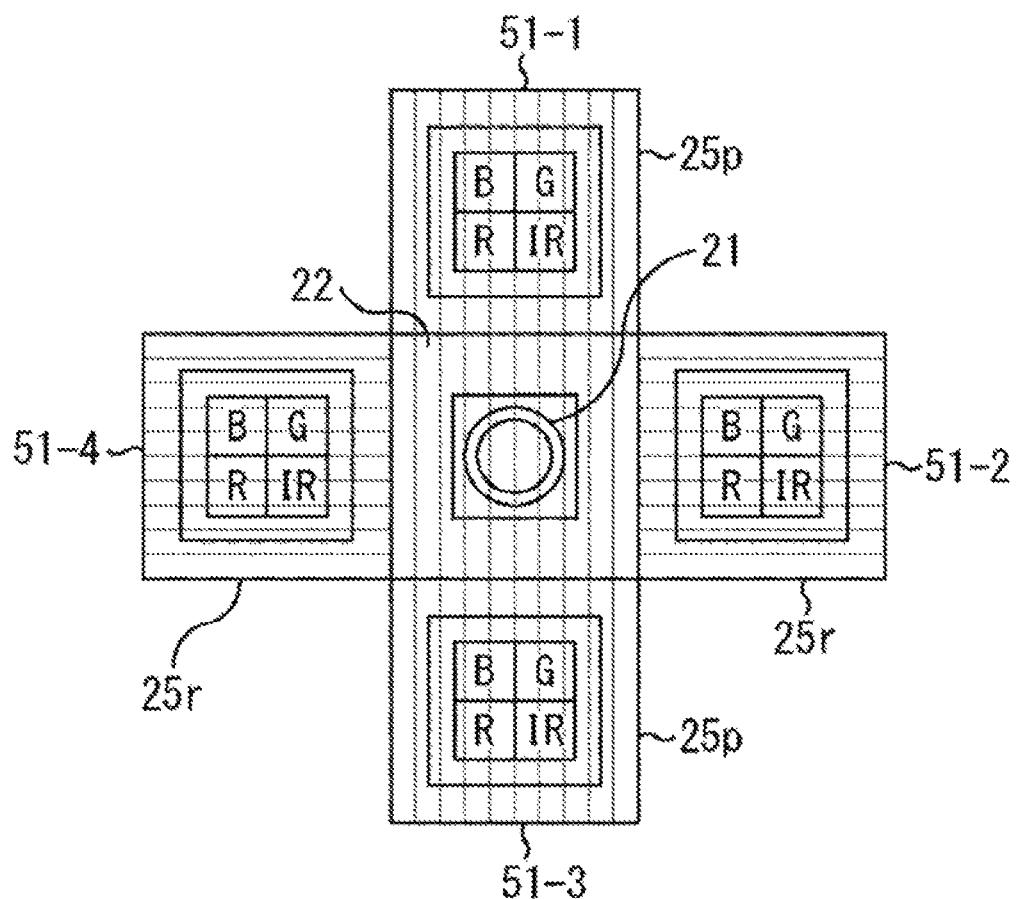
FIG. 8 illustrates a first arrangement example of light sources forming a planar illumination unit.

FIG. 8 illustrates a first arrangement example of the light sources forming the planar illumination unit 24.

In the first arrangement example, the illumination unit 24 includes four LEDs 51-1 to 51-4, and those LEDs are arranged at equal intervals around an optical axis of the camera 21 serving as a center. For each LED 51, one package including four chips that generate R (red) light, G (green) light, B (blue) light, and IR (infrared radiation) light having different wavelengths, respectively, is employed. In each LED 51, each chip can be independently turned on and turned off.

Polarizers 25p whose polarization direction is in parallel to that of the analyzer 22 arranged in front of the camera 21 are arranged in front of the LEDs 51-1 and 51-3 (in optical paths of irradiation light). The polarizers 25r whose polarization direction is orthogonal to that of the analyzer 22 are arranged in front of the LEDs 51-2 and 51-4.

FIG. 9 shows correspondence between measurement items and ON of the light sources in the first arrangement example illustrated in FIG. 8.

Note that, in FIG. 9, Rr means light that has a wavelength of R and is emitted via the polarizer 25r whose polarization direction is orthogonal to that of the analyzer 22. Rp means light that has the wavelength of R and is emitted via the polarizer 25p whose polarization direction is in parallel to that of the analyzer 22. The same applies to irradiation light having other wavelengths. Also in the following drawings, the above definition is applied.

For example, in order to measure color of skin serving as an analysis target, light equal to white light is emitted by simultaneously turning on Rr, Gr, and Br and Rp, Gp, and Bp. In this case, an image of specular reflection light and diffuse reflection light is captured, and therefore it is possible to acquire an image in a condition close to the naked eye of human.

In order to measure shine, polarized light equal to white light is emitted by turning on Rp, Gp, and Bp whose polarization direction is in parallel to that of the analyzer 22. In this case, only an image of specular reflection light is captured while diffuse reflection light is not being generated. Therefore, it is possible to acquire an image of shine which is reflection of a skin surface.

In order to measure pores, only Gr whose polarization direction is orthogonal to that of the analyzer 22 is turned on. With this, only an image of diffuse reflection light reflected by the pores which are an internal structure of skin is captured. Note that, in the example of FIG. 9, the reason why a wavelength of emitted light is G is that sensitivity of the camera 21 is high, as compared with the case of other wavelengths. However, Rr, Br, or IRr may be turned on instead of Gr.

In order to measure skin texture, only Gp whose polarization direction is in parallel to that of the analyzer 22 is turned on. With this, only an image of specular reflection light showing a state of texture which is a surface structure of skin is captured. Note that, in the example of FIG. 9, the reason why a wavelength of emitted light is G is that sensitivity of the camera 21 is high, as compared with the case of other wavelengths. However, Rp, Bp, or IRp may be turned on instead of Gp.

In order to measure an internal melanin index, first, an image of diffuse reflection light of red light whose reflection degree is changed on the basis of presence/absence of an internal melanin pigment is captured in a state in which only Rr whose polarization direction is orthogonal to that of the analyzer 22 is on, and thus a red image is acquired. Then, an image of diffuse reflection light of infrared radiation whose reflection degree is hardly changed on the basis of presence/absence of the internal melanin pigment is captured in a state in which only IRr whose polarization direction is orthogonal to that of the analyzer 22 is on, and thus an infrared image is captured. In the image analysis unit 14, an amount of the internal melanin pigment and distribution thereof are analyzed on the basis of a difference between the red image and the infrared image. Note that measurement of the internal melanin pigment is used to predict a melanin pigment to appear in a stratum corneum in the future.

In order to measure a surface melanin index, first, an image of specular reflection light of red light whose reflection degree is changed on the basis of presence/absence of a melanin pigment on a surface (in a stratum corneum) is captured in a state in which only Rp whose polarization direction is in parallel to that of the analyzer 22 is on, and thus a red image is acquired. Then, an image of specular reflection light of infrared radiation whose reflection degree is hardly changed on the basis of presence/absence of the melanin pigment on the surface is captured in a state in which only IRp whose polarization direction is in parallel to that of the analyzer 22 is on, and thus an infrared image is captured. In the image analysis unit 14, an amount of the melanin pigment on the surface and distribution thereof are analyzed on the basis of a difference between the red image and the infrared image.

In order to measure an internal erythema index, first, an image of diffuse reflection light of red light is captured in a state in which only Rr whose polarization direction is orthogonal to that of the analyzer 22 is on, and thus a red image is acquired. Then, an image of diffuse reflection light of green light is captured in a state in which only Gr whose polarization direction is orthogonal to that of the analyzer 22 is on, and thus a green image is acquired. Hemoglobin that causes erythema absorbs green light well and hardly absorbs red light, and therefore the image analysis unit 14 analyzes an amount of internal hemoglobin and distribution thereof on the basis of a difference between the green image and the red image. Note that measurement of internal hemoglobin is used to observe a state of a capillary vessel in the dermis.

In order to measure a surface erythema index, first, an image of specular reflection light of red light is captured in a state in which only Rp whose polarization direction is in parallel to that of the analyzer 22 is on, and thus a red image is acquired. Then, an image of specular reflection light of green light is captured in a state in which only Gp whose polarization direction is in parallel to that of the analyzer 22 is on, and thus a green image is acquired. The image analysis unit 14 analyzes an amount of surface hemoglobin and distribution thereof on the basis of a difference between the green image and the red image. Note that measurement of surface hemoglobin is used to observe a state of a capillary vessel in the vicinity of epidermis.

Second Arrangement Example of Light Sources Forming Illumination Unit 24

Figure 10:
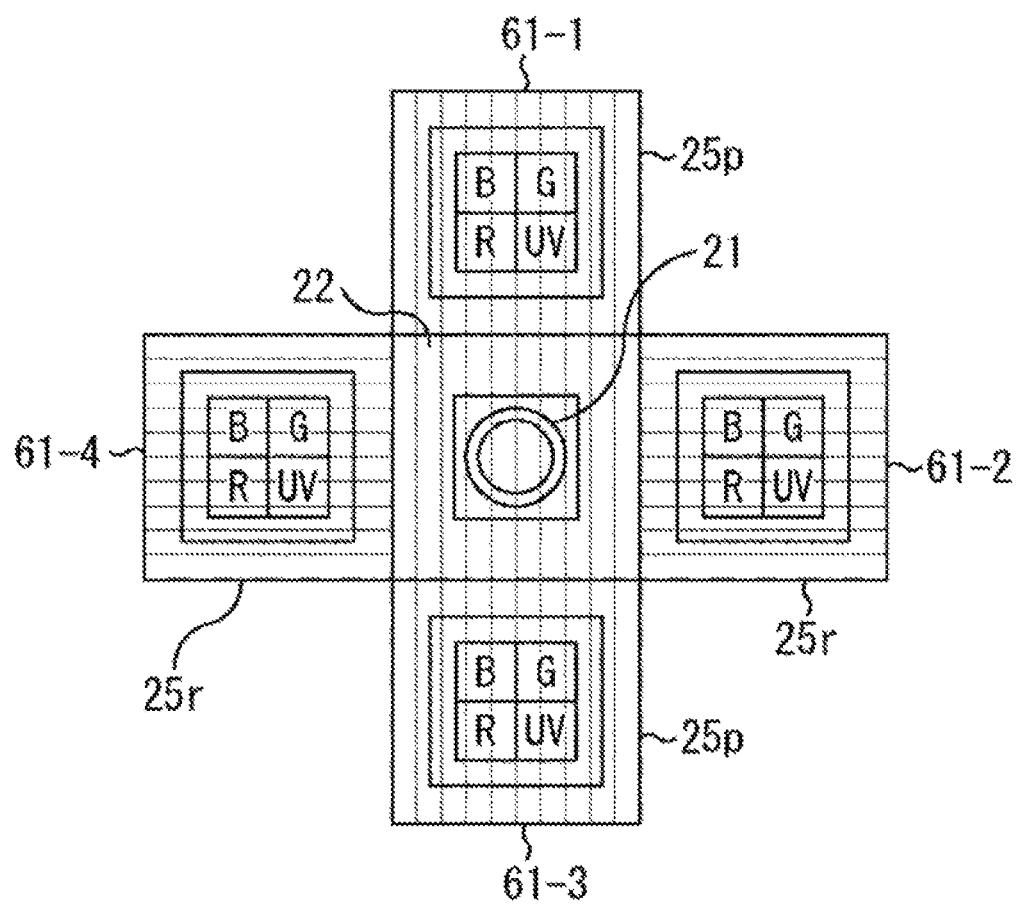
FIG. 10 illustrates a second arrangement example of light sources forming a planar illumination unit.

FIG. 10 illustrates a second arrangement example of the light sources forming the planar illumination unit 24.

In the second arrangement example, the illumination unit 24 includes four LEDs 61-1 to 61-4, and those LEDs are arranged at equal intervals around the optical axis of the camera 21 serving as a center. For each LED 61, one package including four chips that generate R, G, B, and UV (ultraviolet rays) light having different wavelengths, respectively, is employed. In each LED 61, each chip can be independently turned on and turned off.

The polarizers 25p whose polarization direction is in parallel to that of the analyzer 22 arranged in front of the camera 21 are arranged in front of the LEDs 61-1 and 61-3. The polarizers 25r whose polarization direction is orthogonal to that of the analyzer 22 are arranged in front of the LEDs 61-2 and 61-4.

That is, in the second arrangement example, the UV chips are used instead of the IR chips included in the LEDs 51 in the first arrangement example in FIG. 8. With this, although the melanin index cannot be measured, porphyrin can be measured by using fluorescence excitation of UV light instead.

FIG. 11 shows correspondence between measurement items and ON of the light sources in the second arrangement example illustrated in FIG. 10.

Measurement of color, shine, pores, texture, an internal erythema index, and a surface erythema index of skin serving as an analysis target is similar to the case of the above first arrangement example.

In order to measure porphin, the UV chips of all the LEDs 61-1 to 61-4, i.e., UVr whose polarization direction is orthogonal to that of the analyzer 22 and UVp whose polarization direction is in parallel to that of the analyzer 22 are turned on. With this, an image of fluorescence in a visible light range having wavelengths of 600 to 650 nm emitted by porphin in response to emission of ultraviolet rays (UV) is captured.

Third Arrangement Example of Light Sources Forming Illumination Unit 24

Figure 12:
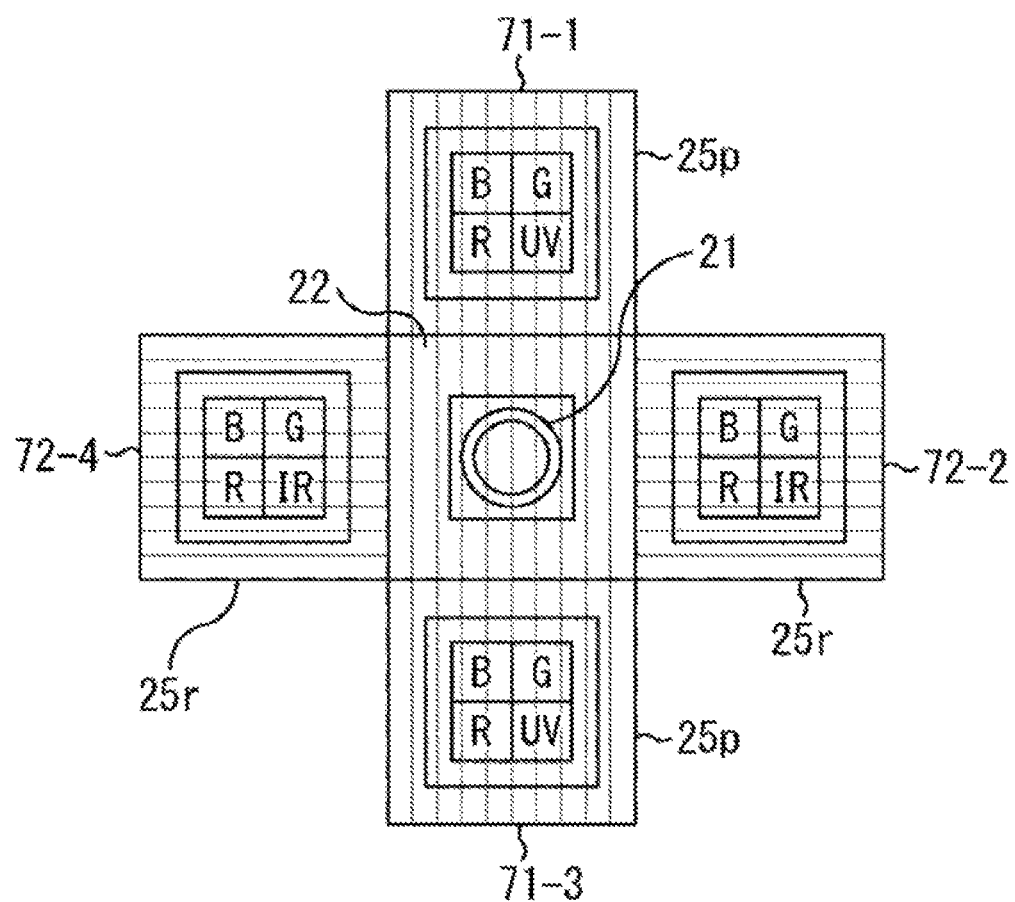
FIG. 12 illustrates a third arrangement example of light sources forming a planar illumination unit.

FIG. 12 illustrates a third arrangement example of the light sources forming the planar illumination unit 24.

In the third arrangement example, the illumination unit 24 includes four LEDs 71-1, 71-3, 72-2, and 72-4, and those LEDs are arranged at equal intervals around the optical axis of the camera 21 serving as a center. For each of the LEDs 71-1 and 71-3, one package including four chips that generate R, G, B, and UV light having different wavelengths, respectively, is employed. The polarizers 25p whose polarization direction is in parallel to that of the analyzer 22 are arranged in front of the LEDs 71-1 and 71-3 (in optical paths of irradiation light).

For each of the LEDs 72-2 and 72-4, one package including four chips that generate R, G, B, and IR light having different wavelengths, respectively, is employed. The polarizers 25r whose polarization direction is orthogonal to that of the analyzer 22 are arranged in front of the LEDs 72-2 and 72-4.

Note that each internal chip of the LEDs 71 and 72 can be independently turned on and turned off.

That is, the third arrangement example is a combination of the first arrangement example in FIG. 8 and the second arrangement example in FIG. 10, and color, shine, pores, texture, an internal melanin index, an internal erythema index, a surface erythema index, and porphin of skin serving as an analysis target can be measured.

FIG. 13 shows correspondence between measurement items and ON of the light sources in the third arrangement example illustrated in FIG. 12.

Measurement of color, shine, pores, texture, an internal melanin index, an internal erythema index, and a surface erythema index of skin serving as an analysis target is similar to the case of the above first example configuration. Measurement of porphin is similar to the case of the above second example configuration.

Fourth Arrangement Example of Light Sources Forming Illumination Unit 24

Figure 14:
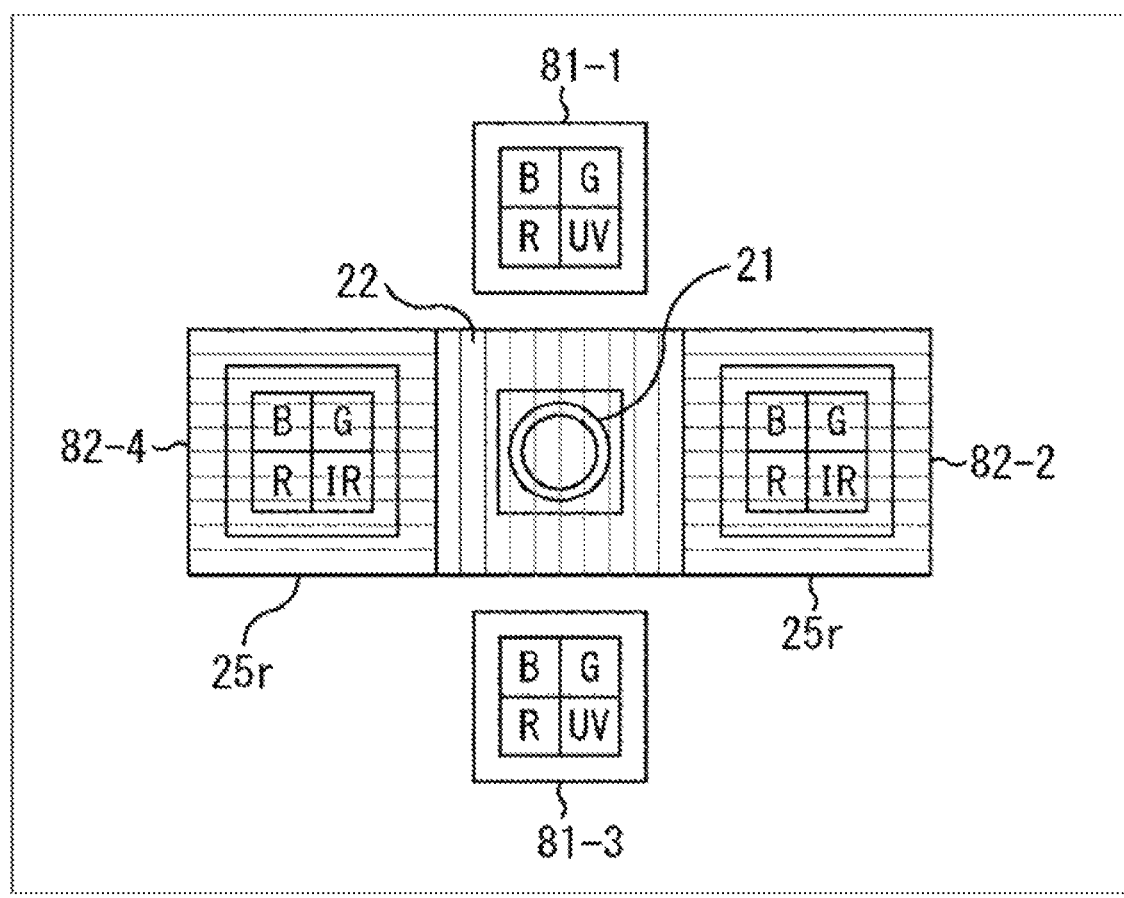
FIG. 14 illustrates a fourth arrangement example of light sources forming a planar illumination unit.

FIG. 14 illustrates a fourth arrangement example of the light sources forming the planar illumination unit 24.

In the fourth arrangement example, the illumination unit 24 includes four LEDs 81-1, 81-3, 82-2, and 82-4, and those LEDs are arranged at equal intervals around the optical axis of the camera 21 serving as a center. For each of the LEDs 81-1 and 81-3, one package including four chips of R, G, B, and UV having different wavelengths, respectively, is employed.

For each of the LEDs 82-2 and 82-4, one package including four chips of R, G, B, and IR having different wavelengths, respectively, is employed. The polarizers 25r whose polarization direction is orthogonal to that of the analyzer 22 are arranged in front of the LEDs 82-2 and 82-4.

Note that each internal chip of the LEDs 81 and 82 can be independently turned on and turned off.

That is, the fourth arrangement example is obtained by omitting, from the third arrangement example in FIG. 12, the polarizers 25p whose polarization direction is in parallel to that of the analyzer 22. In the case of the fourth arrangement example, irradiation light whose polarization direction is in parallel to that of the analyzer 22 cannot be emitted, and therefore a state of a skin surface cannot be intensively measured. Therefore, although shine and texture of skin can be measured in the fourth arrangement example, ability thereof is inferior to that of the first arrangement example in FIG. 8, for example.

FIG. 15 shows correspondence between measurement items and ON of the light sources in the fourth arrangement example illustrated in FIG. 14.

Measurement of color, shine, pores, texture, an internal melanin index, an erythema index, and porphyrin of skin serving as an analysis target is similar to the case of any of the above first to third arrangement examples.

Fifth Arrangement Example of Light Sources Forming Illumination Unit 24

Figure 16:
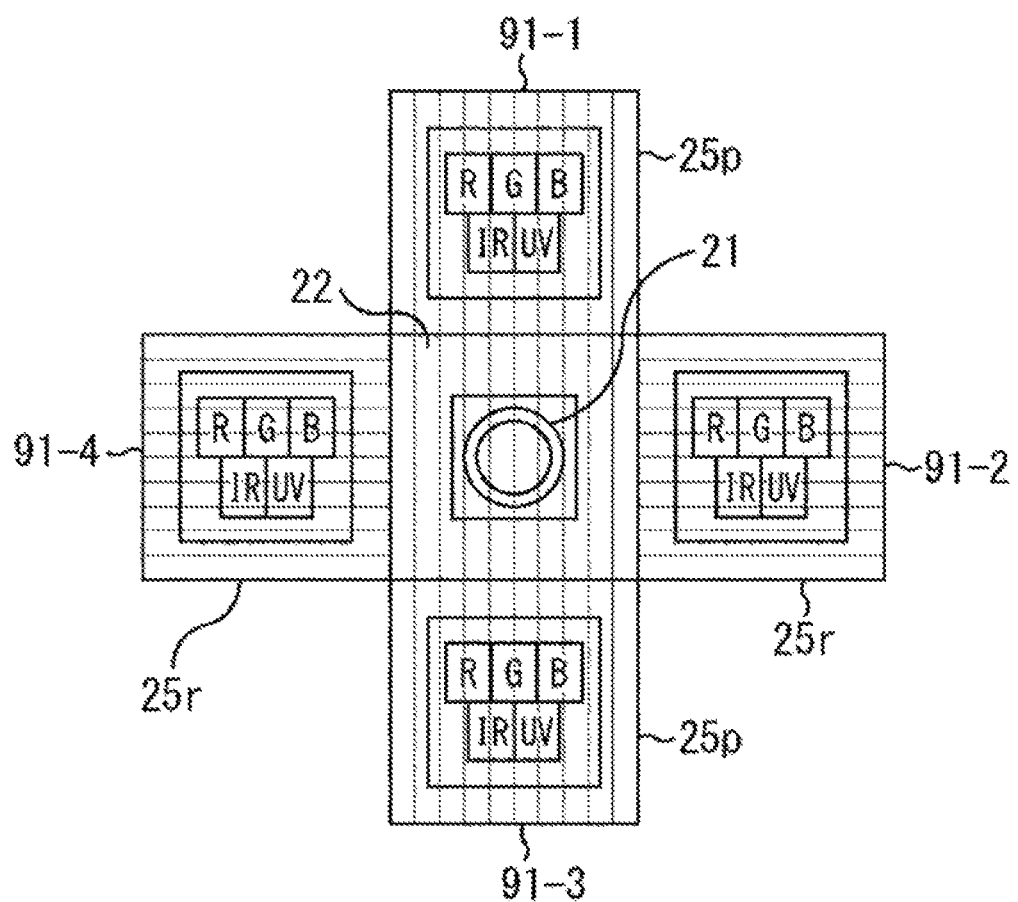
FIG. 16 illustrates a fifth arrangement example of light sources forming a planar illumination unit.

FIG. 16 illustrates a fifth arrangement example of the light sources forming the planar illumination unit 24.

In the fifth arrangement example, the illumination unit 24 includes four LEDs 91-1 to 91-4, and those LEDs are arranged at equal intervals around the optical axis of the camera 21 serving as a center. For each of the LEDs 91-1 to 91-4, one package including five chips that generate R, G, B, IR, and UV light having different wavelengths, respectively, is employed. In each LED 91, each internal chip can be independently turned on and turned off.

The polarizers 25p whose polarization direction is in parallel to that of the analyzer 22 are arranged in front of the LEDs 91-1 and 91-3. The polarizers 25r whose polarization direction is orthogonal to that of the analyzer 22 are arranged in front of the LEDs 91-2 and 91-4.

FIG. 17 shows correspondence between measurement items and ON of the light sources in the fifth arrangement example illustrated in FIG. 15.

Measurement of color, shine, pores, texture, an internal melanin index, a surface melanin index, an internal erythema index, a surface erythema index, and porphyrin of skin serving as an analysis target is similar to the case of any one of the above first to fourth arrangement examples.

Sixth Arrangement Example of Light Sources Forming Illumination Unit 24

Figure 18:
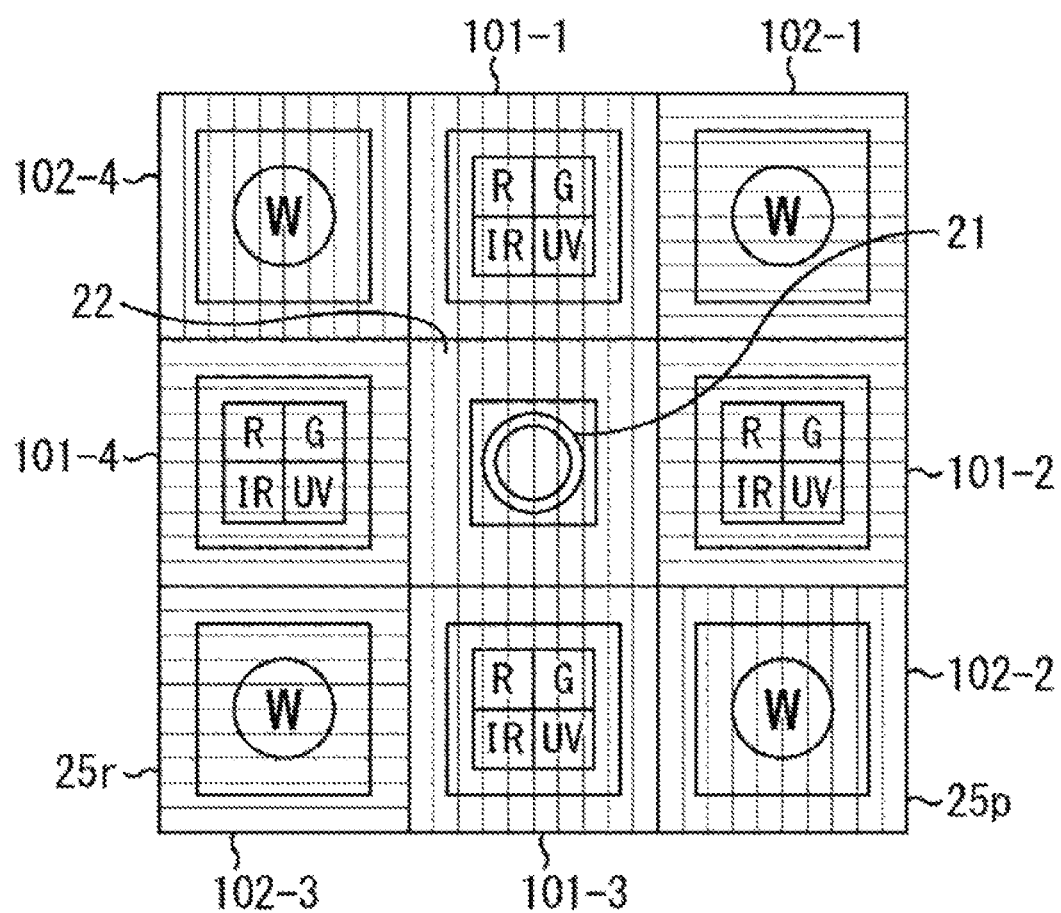
FIG. 18 illustrates a sixth arrangement example of light sources forming a planar illumination unit.

FIG. 18 illustrates a sixth arrangement example of the light sources forming the planar illumination unit 24.

In the sixth arrangement example, the illumination unit 24 includes eight LEDs 101-1 to 101-4 and 102-1 to 102-4, and those LEDs are arranged at equal intervals around the optical axis of the camera 21 serving as a center. For each of the LEDs 101-1 to 101-4, one package including four chips that generate R, G, IR, and UV light having different wavelengths, respectively, is employed. In each LED 101, each internal chip can be independently turned on and turned off. For each of the LEDs 102-1 to 102-4, an LED that generates W light (white light) is employed.

The polarizers 25p whose polarization direction is in parallel to that of the analyzer 22 are arranged in front of the LEDs 101-1, 101-3, 102-2, and 102-4. The polarizers 25r whose polarization direction is orthogonal to that of the analyzer 22 are arranged in front of the LEDs 101-2, 101-4, 102-1, and 102-3.

FIG. 19 shows correspondence between measurement items and ON of the light sources in the sixth arrangement example illustrated in FIG. 18.

For example, in order to measure color of skin serving as an analysis target, Wr and Wp are turned on. With this, an image of specular reflection light and diffuse reflection light of white light is captured, and therefore it is possible to acquire an image in a condition close to the naked eye of human.

In order to measure shine, Wp that is polarization light in parallel to the analyzer 22 is turned on. With this, only an image of specular reflection light of white light is captured while diffuse reflection light thereof is not being generated. Therefore, it is possible to acquire an image of shine which is reflection of a skin surface.

Measurement of other items is similar to the case of any one of the above first to fifth example configurations.

Seventh Arrangement Example of Light Sources Forming Illumination Unit 24

Figure 20:
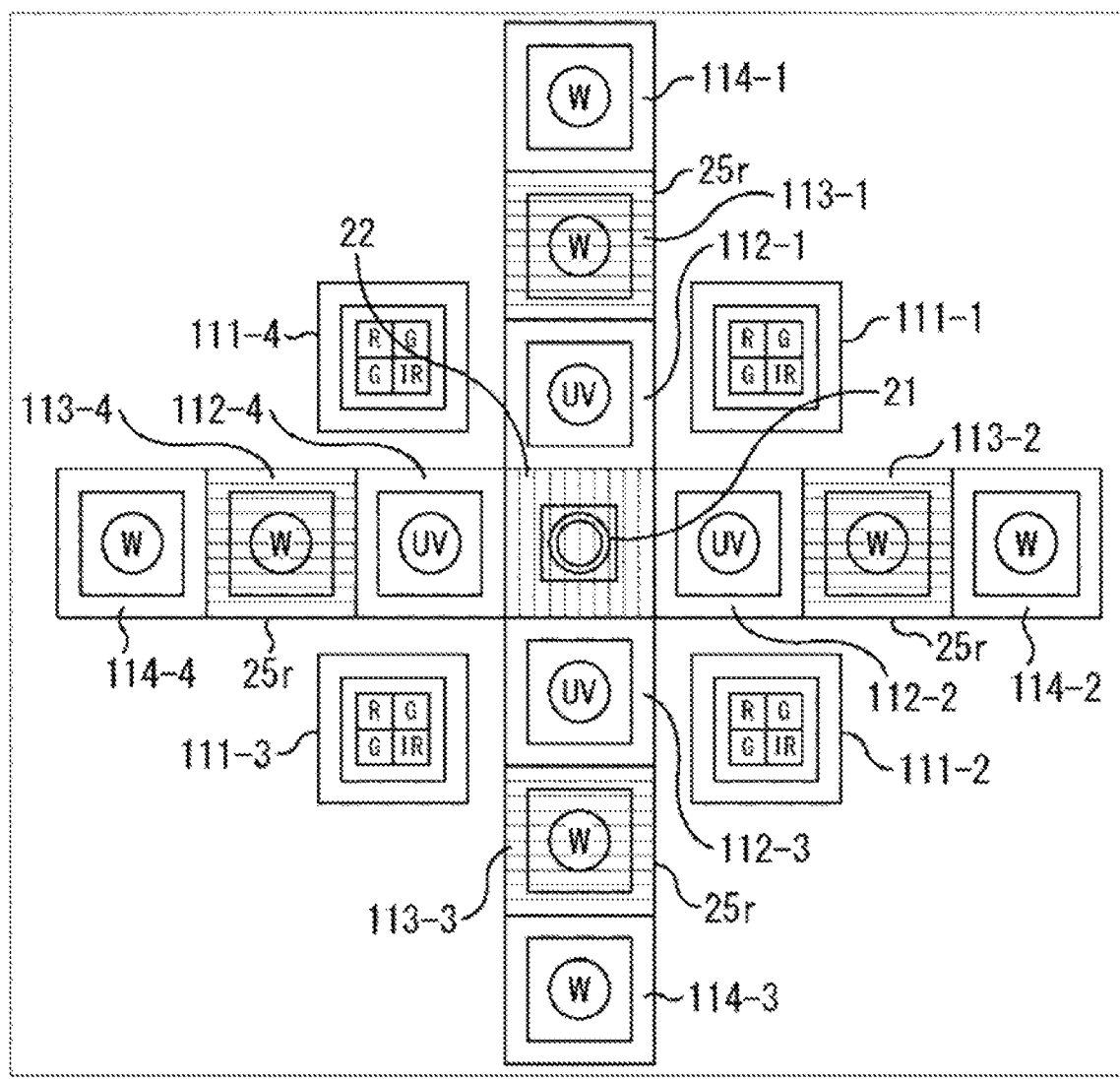
FIG. 20 illustrates a seventh arrangement example of light sources forming a planar illumination unit.

FIG. 20 illustrates a seventh arrangement example of the light sources forming the planar illumination unit 24.

In the seventh arrangement example, the illumination unit 24 includes sixteen LEDs 111-1 to 111-4, 112-1 to 112-4, 113-1 to 113-4, and 114-1 to 114-4, and those LEDs are arranged at equal intervals around the optical axis of the camera 21 serving as a center.

For each of the LEDs 111-1 to 111-4, one package including four chips that generate R, G, G, and IR light having different wavelengths, respectively, is employed. Note that two G chips are provided in one package because light emission output thereof is smaller than that of R and other chips. In each LED 111, the R, G, and IR chips can be independently turned on and turned off.

For the LEDs 112-1 to 112-4, LEDs that generate UV light are employed.

For the LEDs 113-1 to 113-4, LEDs that generate W light are employed. The polarizers 25r whose polarization direction is orthogonal to that of the analyzer 22 are arranged in front of the respective LEDs 113.

For the LED 114-1 to 114-4, LEDs that generate W light are employed.

FIG. 21 shows correspondence between measurement items and ON of the light sources in the seventh arrangement example illustrated in FIG. 20.

Measurement of color, pores, texture, a melanin index, an erythema index, and porphyrin of skin serving as an analysis target is similar to the case of any one of the above first to sixth examples.

The first to seventh arrangement examples of the light sources forming the illumination unit 24 described above can be combined with any one of the first to third example configurations of the image acquisition unit 13.

Fourth Example Configuration of Image Acquisition Unit 13

Figure 22:
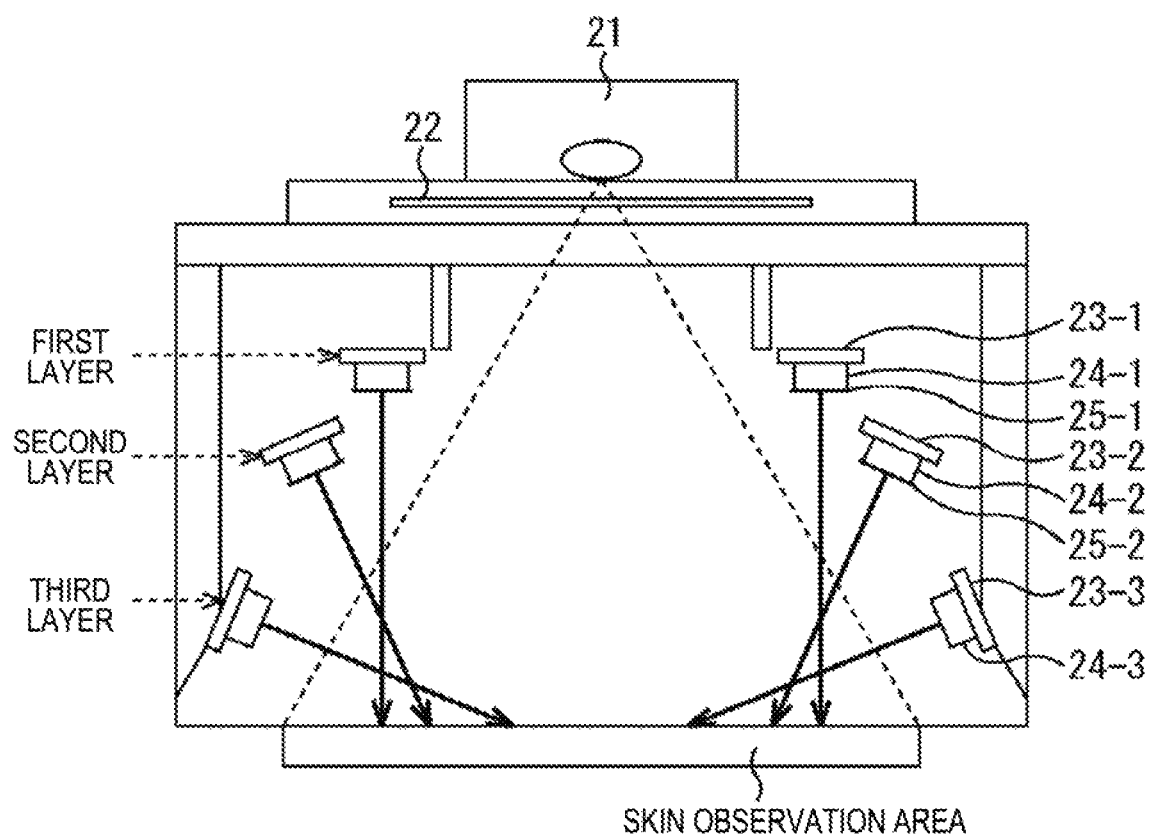
FIG. 22 is a cross-sectional view illustrating a fourth example configuration of an image acquisition unit in FIG. 4.

FIG. 22 illustrates a cross-section of a fourth example configuration of the image acquisition unit 13. The fourth example configuration includes the camera 21, the analyzer 22, and the PCBs 23, the illumination units 24, and the polarizers 25 which are three-dimensionally arranged to be divided into three layers.

As illustrated in FIG. 22, in the fourth example configuration, the PCBs 23, the illumination units 24, and the polarizers 25 are divided into three layers and are three-dimensionally arranged. That is, a first layer includes a PCB 23-1, an illumination unit 24-1, and a polarizer 25-1. A second layer includes a PCB 23-2, an illumination unit 24-2, and a polarizer 25-2. A third layer includes a PCB 23-3 and an illumination unit 24-2.

The illumination units 24-1 to 24-3 are arranged at different angles so that irradiation directions thereof face an analysis target.

The polarizers 25-1 and 25-2 are arranged in front of the illumination units 24-1 and 24-2, respectively. Note that the polarizer 25-1 or 25-2 may be omitted or a polarizer may be arranged in front of the illumination unit 24-3.

The illumination units 24-1 to 24-3 are three-dimensionally arranged, and therefore a size of the image acquisition unit 13 can be reduced in the fourth example configuration, as compared with the above first to third example configurations. Note that, when the illumination units 24 are three-dimensionally formed, the illumination units 24 may be three layers as illustrated in FIG. 22 or may have two layers or four or more layers.

Eighth Arrangement Example of Light Sources Forming Illumination Units 24-1 to 24-3

Figure 23:
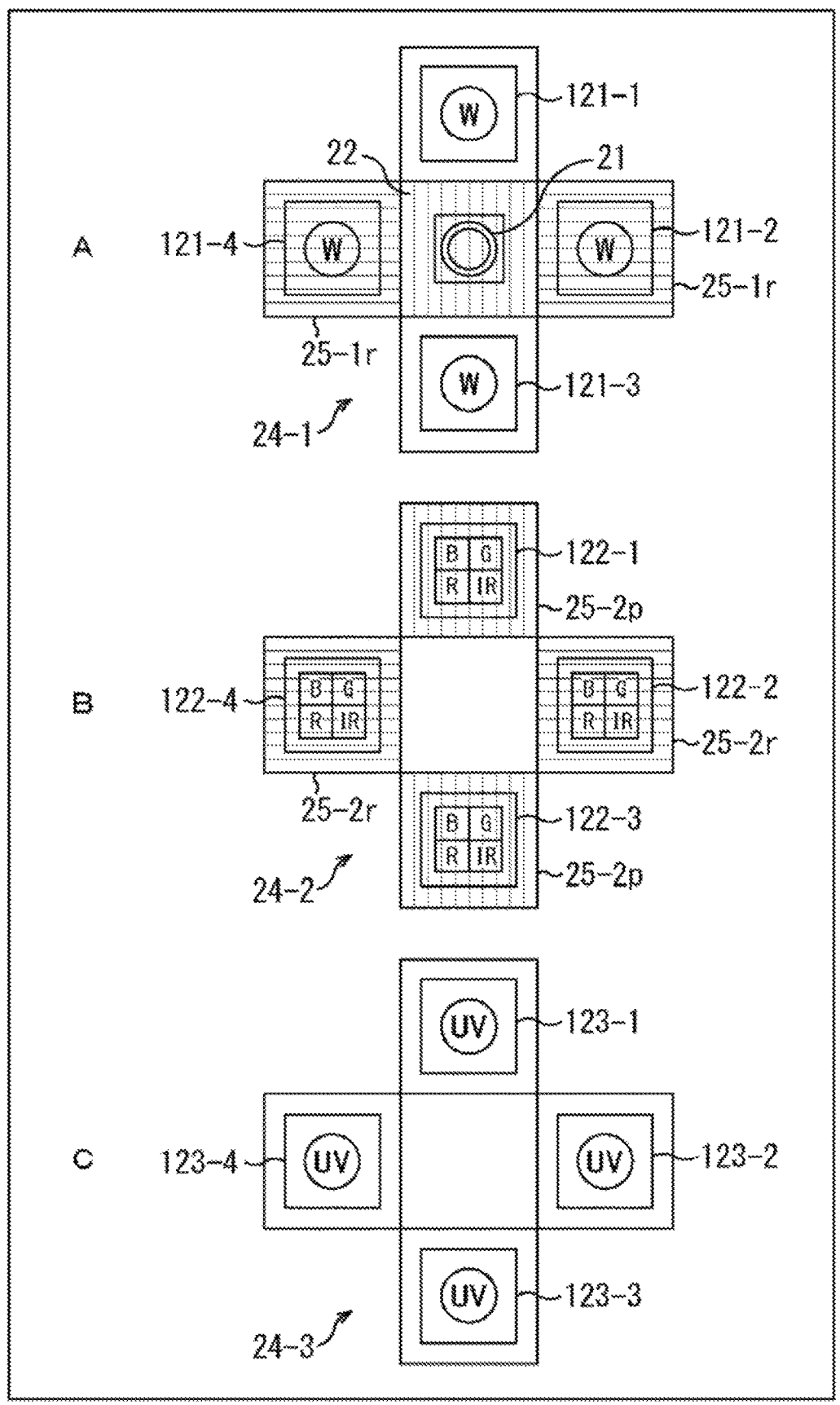
FIG. 23 illustrates an eighth arrangement example of light sources forming an illumination unit in FIG. 22.

FIG. 23 illustrates an arrangement example (hereinafter, referred to as "eighth arrangement example") of light sources forming the three-dimensional illumination units 24-1 to 24-3 in FIG. 22.

As illustrated in FIG. 23A, the illumination unit 24-1 arranged in the first layer includes four LEDs 121-1 to 121-4, and those LEDs are arranged at equal intervals around the optical axis of the camera 21 serving as a center.

For each LED 121, an LED that generates W light (white light) is employed. Polarizers 25-1r whose polarization direction is orthogonal to that of the analyzer 22 arranged in front of the camera 21 are arranged in front of the LEDs 121-2 and 121-4.

As illustrated in FIG. 23B, the illumination unit 24-2 arranged in the second layer includes four LEDs 122-1 to 122-4, and those LEDs are arranged at equal intervals around the optical axis of the camera 21 serving as a center. For each LED 122, one package including four chips that generate R, G, B, and IR light having different wavelengths, respectively, is employed. In each LED 122, each chip can be independently turned on and turned off. Polarizers 25-2p whose polarization direction is in parallel to that of the analyzer 22 arranged in front of the camera 21 are arranged in front of the LEDs 122-1 and 121-3. Polarizers 25-2r whose polarization direction is orthogonal to that of the analyzer 22 arranged in front of the camera 21 are arranged in front of the LEDs 122-2 and 122-4.

As illustrated in FIG. 23C, the illumination unit 24-3 arranged in the third layer includes four LEDs 123-1 to 123-4, and those LEDs are arranged at equal intervals around the optical axis of the camera 21 serving as a center. For each LED 123, an LED that generates UV light is employed.

Note that the illumination units 24-1 to 24-3 can be rotated around the optical axis of the camera 21, and the illumination unit 24-2 in the second layer is arranged at a position where light emitted therefrom is not blocked by the illumination unit 24-3 in the third layer. Similarly, the illumination unit 24-1 in the first layer is arranged at a position where light emitted therefrom is not blocked by the illumination unit 24-2 in the second layer or the illumination unit 24-3 in the third layer.

Note that, in the case of the eighth arrangement example, an LED having relatively small output is arranged in a layer closer to a skin observation area (for example, a UV LED having relatively small output is arranged in the third layer, and a W LED having relatively large output is arranged in the first layer). However, the arrangement is not limited to the example illustrated in FIG. 8 but is arbitrary.

FIG. 24 shows correspondence between measurement items and ON of the light sources in the eighth arrangement example illustrated in FIG. 23.

Measurement of color, shine, pores, texture, an internal melanin index, a surface melanin index, an internal erythema index, a surface erythema index, and porphin of skin serving as an analysis target is similar to the case of any one of the above first to seventh examples.

Fifth Example Configuration of Image Acquisition Unit 13

Figure 25:
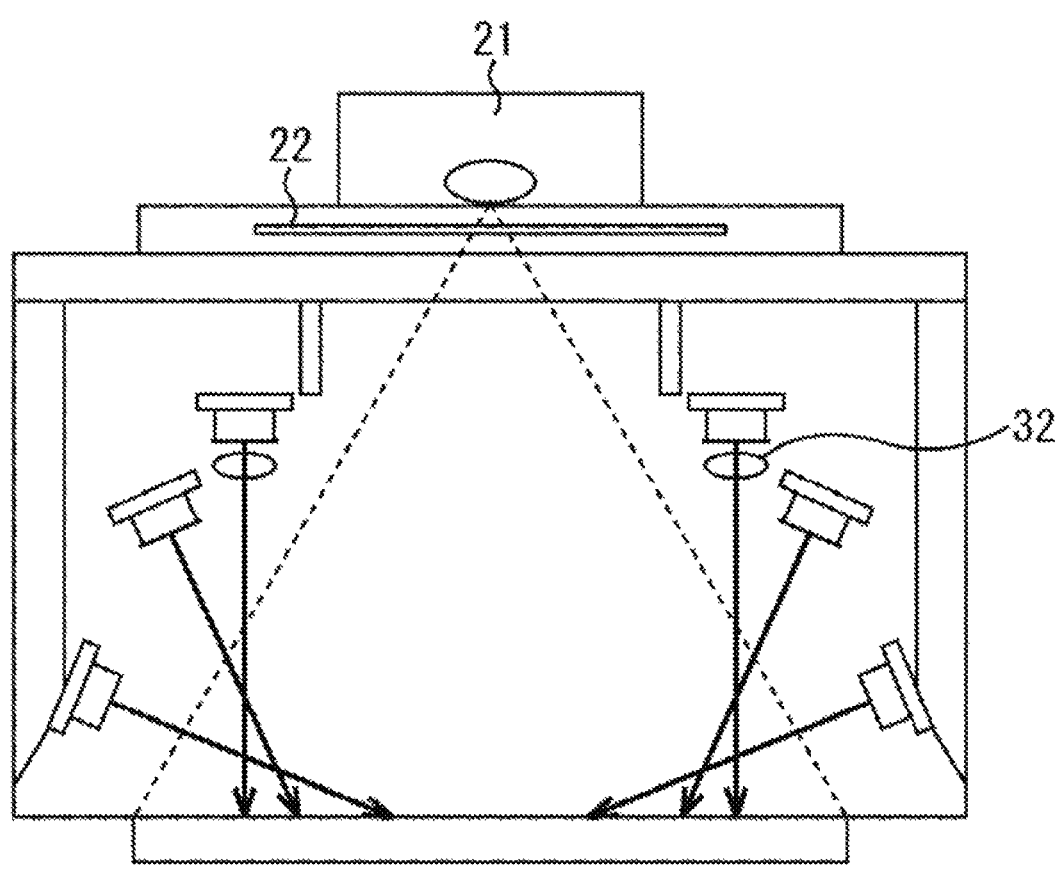
FIG. 25 is a cross-sectional view illustrating a fifth example configuration of an image acquisition unit in FIG. 4.

FIG. 25 illustrates a cross-section of a fifth example configuration of the image acquisition unit 13. In the fifth example configuration, lenses 32 serving as light guide members are arranged in front of the illumination unit 24-1 in the first layer in the fourth example configuration illustrated in FIG. 22. Note that constituent elements common to the fourth example configuration are denoted by the same numbers, and therefore description thereof is omitted.

Regarding an arrangement example of the light sources forming the illumination units 24-1 to 24-3, not only the eighth arrangement example illustrated in FIG. 23 but also arbitrary arrangement can be employed.

The lenses 32 are curved in a travelling direction of irradiation light emitted by the illumination unit 24-1 to irradiate the skin observation area. Because the lenses 32 are arranged, it is possible to efficiently irradiate the skin observation area with irradiation light emitted by the illumination unit 24-1.

Note that a central axis of (the light sources included in) the illumination unit 24-1 and a central axis of the lens 32 do not necessarily correspond to each other. Instead, irradiation light can be emitted more efficiently in some cases by decentering both the central axes.

Note that the lenses 32 may be arranged in front of at least one of the illumination units 24-2 and 24-3 instead of or in addition to the lenses arranged in front of the illumination unit 24-1.

Sixth Example Configuration of Image Acquisition Unit 13

Figure 26:
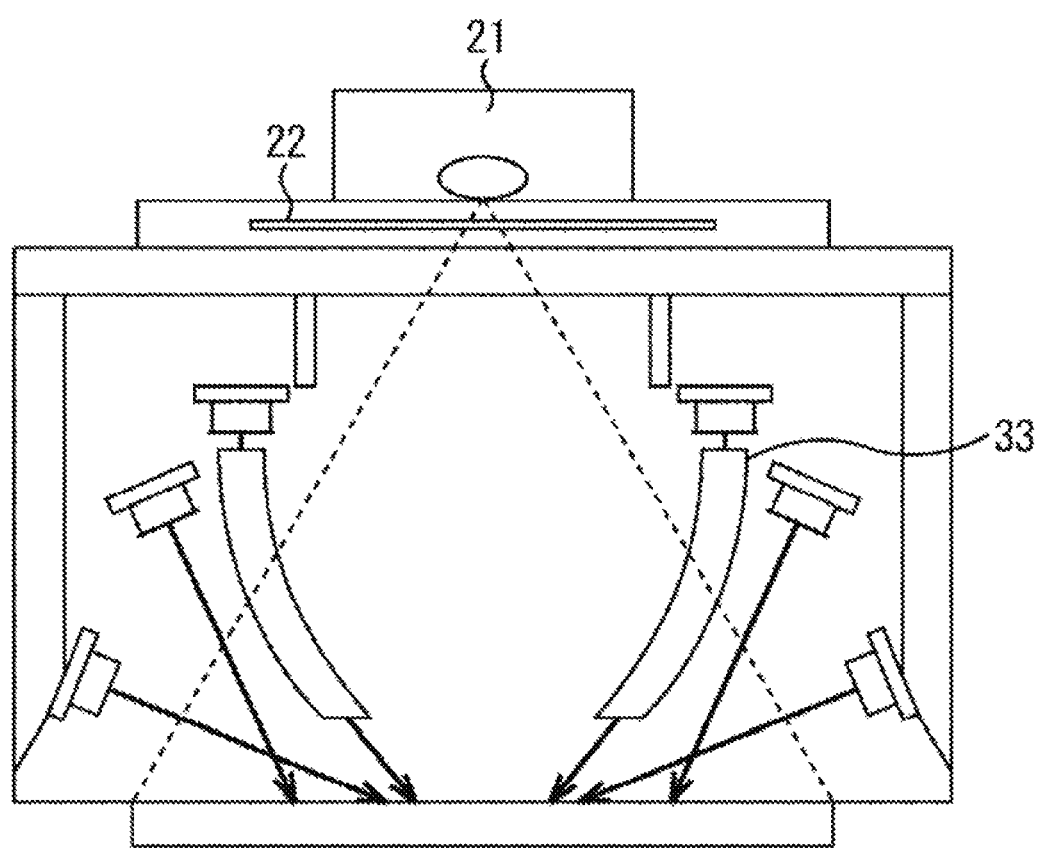
FIG. 26 is a cross-sectional view illustrating a sixth example configuration of an image acquisition unit in FIG. 4.

FIG. 26 illustrates a cross-section of a sixth example configuration of the image acquisition unit 13. In the sixth example configuration, light pipes 33 serving as light guide members are arranged in front of the illumination unit 24-1 in the first layer in the fourth example configuration illustrated in FIG. 22. Note that constituent elements common to the fourth example configuration are denoted by the same numbers, and therefore description thereof is omitted.

Regarding an arrangement example of the light sources forming the illumination units 24-1 to 24-3, not only the eighth arrangement example illustrated in FIG. 23 but also arbitrary arrangement can be employed.

The light pipes 33 are curved in a travelling direction of irradiation light emitted by the illumination unit 24-1 to irradiate the skin observation area. Because the light pipes 33 are arranged, it is possible to efficiently irradiate the skin observation area with irradiation light emitted by the illumination unit 24-1.

Note that a central axis of (the light sources included in) the illumination unit 24-1 and a central axis of the light pipe 33 do not necessarily correspond to each other. Instead, irradiation light can be emitted more efficiently in some cases by decentering both the central axes.

Note that the light pipes 33 may be arranged in front of at least one of the illumination units 24-2 and 24-3 instead of or in addition to the lenses arranged in front of the illumination unit 24-1.

Seventh Example Configuration of Image Acquisition Unit 13

Figure 27:
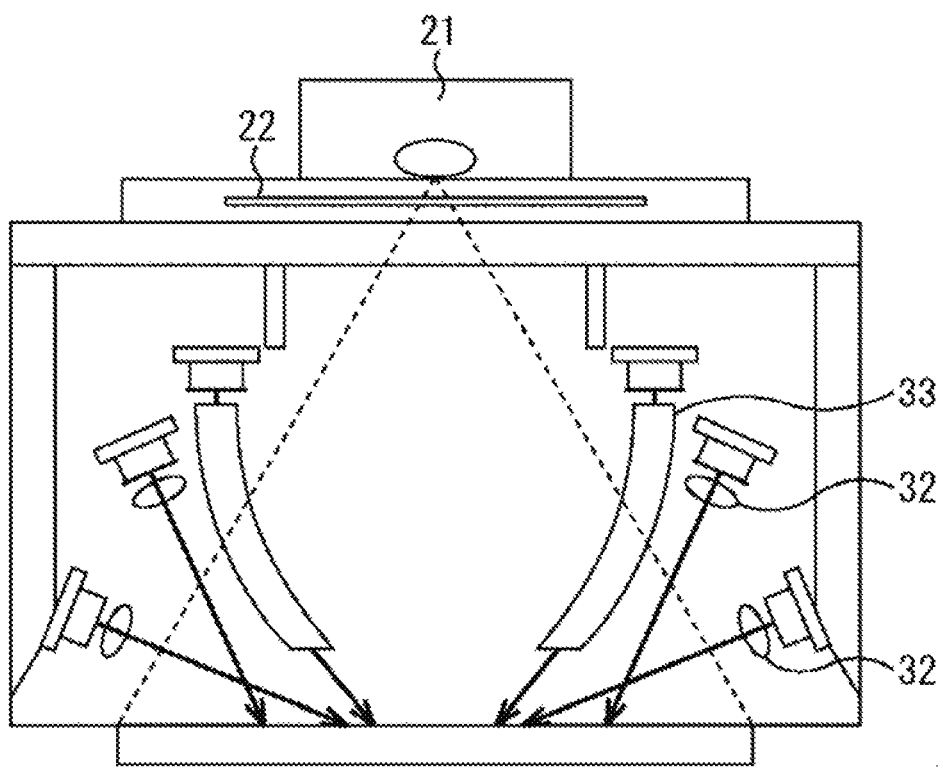
FIG. 27 is a cross-sectional view illustrating a seventh example configuration of an image acquisition unit in FIG. 4.

FIG. 27 illustrates a cross-section of a seventh example configuration of the image acquisition unit 13. In the seventh example configuration, the light pipes 33 serving as the light guide members are arranged in front of the illumination unit 24-1 in the first layer, and the lenses 32 serving as the light guide members are arranged in front of the illumination unit 24-2 in the second layer and the illumination unit 24-3 in the third layer in the fourth example configuration illustrated in FIG. 22. Note that constituent elements common to the fourth to sixth example configurations are denoted by the same numbers, and therefore description thereof is omitted.

Regarding an arrangement example of the light sources forming the illumination units 24-1 to 24-3, not only the eighth arrangement example illustrated in FIG. 23 but also arbitrary arrangement can be employed.

The lenses 32 are curved in a travelling direction of irradiation light emitted by the illumination units 24-2 and 24-3 to irradiate the skin observation area. The light pipes 33 are curved in a travelling direction of irradiation light emitted by the illumination unit 24-1 to irradiate the skin observation area. Because the lenses 32 and the light pipes 33 are arranged, it is possible to efficiently irradiate the skin observation area with irradiation light emitted by the illumination units 24-1 to 24-3.

Note that a central axis of the lens 32 or the light pipe 33 and a central axis of (the light sources included in) any one of the corresponding illumination units 24-1 to 24-3 do not necessarily correspond to each other. Instead, irradiation light can be emitted more efficiently in some cases by decentering both the central axes.

Note that the light pipes 33 may be arranged at positions where the lenses 32 may be arranged, or the lenses 32 may be arranged at positions where the light pipes 33 are arranged.

Eighth Example Configuration of Image Acquisition Unit 13

Figure 28:
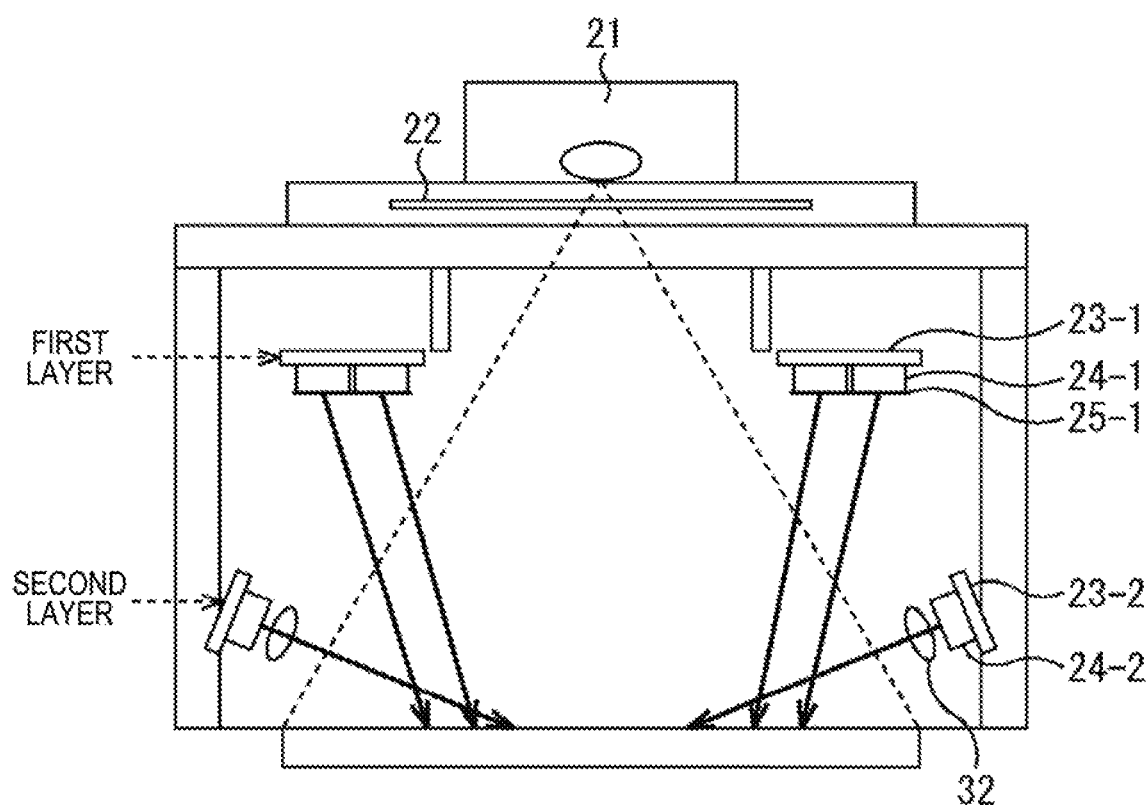
FIG. 28 is a cross-sectional view illustrating an eighth example configuration of an image acquisition unit in FIG. 4.

FIG. 28 illustrates a cross-section of an eighth example configuration of the image acquisition unit 13. The eighth example configuration includes the camera 21, the analyzer 22, and the PCBs 23, the illumination units 24, and the polarizers 25 which are three-dimensionally arranged to be divided into two layers.

As illustrated in FIG. 28, in the eighth example configuration, the PCBs 23, the illumination units 24, and the polarizers 25 are divided into two layers and are three-dimensionally arranged. That is, the first layer includes the PCB 23-1, the illumination unit 24-1, and the polarizer 25-1. The second layer includes the PCB 23-2, the illumination unit 24-2, and the lens 32.

The illumination units 24-1 and 24-2 are arranged at different angles so that irradiation directions thereof face an analysis target.

The illumination units 24-1 and 24-2 are three-dimensionally arranged, and therefore a size of the image acquisition unit 13 can be reduced in the eighth example configuration, as compared with the above first to third example configurations.

Ninth Arrangement Example of Light Sources Forming Illumination Units 24-1 to 24-3

Figure 29:
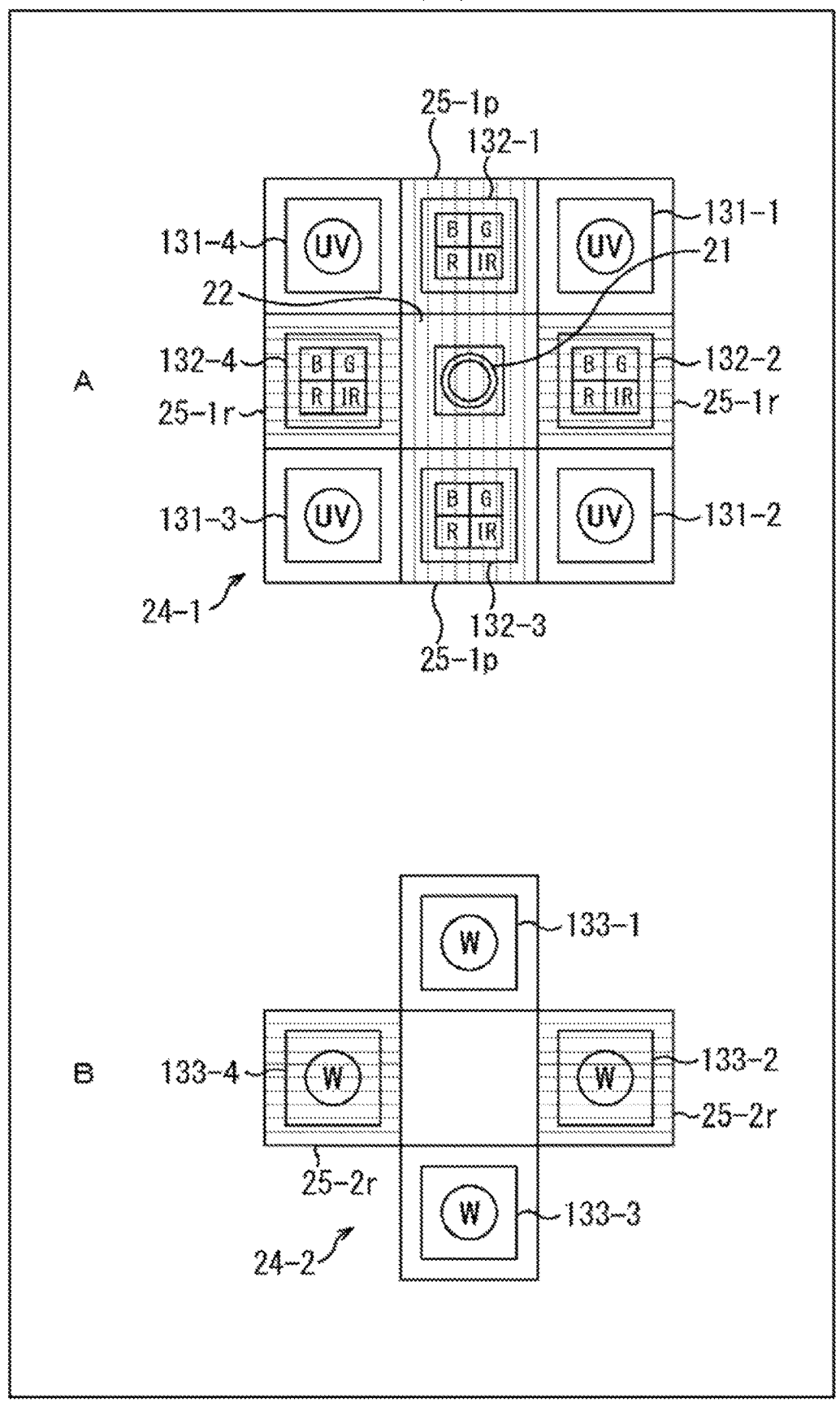
FIG. 29 illustrates a ninth arrangement example of light sources forming an illumination unit in FIG. 28.

FIG. 29 illustrates an arrangement example (hereinafter, referred to as "ninth arrangement example") of light sources forming the three-dimensional illumination units 24-1 and 24-2 in FIG. 28.

As illustrated in FIG. 29A, the illumination unit 24-1 arranged in the first layer includes eight LEDs 131-1 to 131-4 and 132-1 to 132-4, and those LEDs are arranged at equal intervals around the optical axis of the camera 21 serving as a center. For each LED 131, an LED that generates UV light is employed. For each LED 132, one package including four chips that generate R, G, B, and IR light having different wavelengths, respectively, is employed. In each LED 132, each chip can be independently turned on and turned off. Polarizers 25-1p whose polarization direction is in parallel to that of the analyzer 22 arranged in front of the camera 21 are arranged in front of the LEDs 132-1 and 132-3. The polarizers 25-1r whose polarization direction is orthogonal to that of the analyzer 22 arranged in front of the camera 21 are arranged in front of the LEDs 132-2 and 132-4.

As illustrated in FIG. 29B, the illumination unit 24-2 arranged in the second layer includes four LEDs 13-1 to 133-4, and those LEDs are arranged at equal intervals around the optical axis of the camera 21 serving as a center. For each LED 133, an LED that generates W light is employed. The polarizers 25-2r whose polarization direction is orthogonal to that of the analyzer 22 arranged in front of the camera 21 are arranged in front of the LEDs 133-2 and 133-4.

Note that the illumination units 24-1 and 24-2 can be rotated around the optical axis of the camera 21, and the illumination unit 24-1 in the first layer is arranged at a position where light emitted therefrom is not blocked by the illumination unit 24-2 in the second layer.

Note that, in the case of the ninth arrangement example, a large number of LEDs are arranged in the first layer far from the skin observation area, but the large number of LEDs may be arranged in the second layer. Configurations of chips forming an LED and one package are not limited to the examples illustrated in FIG. 29 but are arbitrary.

Correspondence between measurement items and ON of the light sources in the ninth arrangement example is similar to the correspondence between the measurement items and ON of the light sources in the eighth arrangement example described with reference to FIG. 24, and therefore description thereof is omitted.

Ninth Example Configuration of Image Acquisition Unit 13

Figure 30:
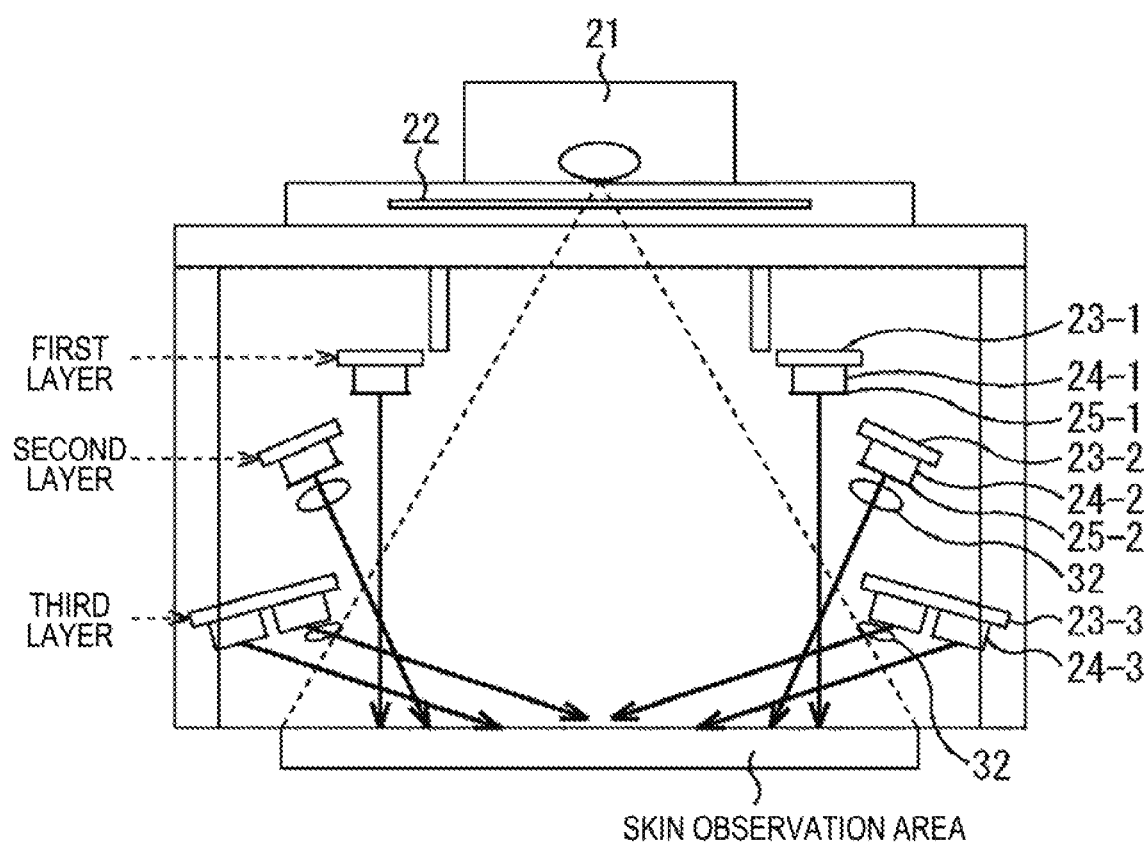
FIG. 30 is a cross-sectional view illustrating a ninth example configuration of an image acquisition unit in FIG. 4.

FIG. 30 illustrates a cross-section of a ninth example configuration of the image acquisition unit 13. The ninth example configuration includes the camera 21, the analyzer 22, and the PCBs 23, the illumination units 24, and the polarizers 25 which are three-dimensionally arranged to be divided into three layers.

As illustrated in FIG. 30, in the ninth example configuration, the PCBs 23, the illumination units 24, and the polarizers 25 are divided into three layers and are three-dimensionally arranged. That is, the first layer includes the PCB 23-1, the illumination unit 24-1, and the polarizer 25-1. The second layer includes the PCB 23-2, the illumination unit 24-2, the polarizer 25-2, and the lens 32. The third layer includes the PCB 23-3, the illumination unit 24-3, and the lens 32. Note that the lens 32 in the third layer is used in a part of the illumination unit 24-3.

The illumination units 24-1 to 24-3 are arranged at different angles so that irradiation directions thereof face an analysis target.

The illumination units 24-1 to 24-3 are three-dimensionally arranged, and therefore a size of the image acquisition unit 13 can be reduced in the ninth example configuration, as compared with the above first to third example configurations.

Tenth Arrangement Example of Light Sources Forming Illumination Units 24-1 to 24-3

Figure 31:
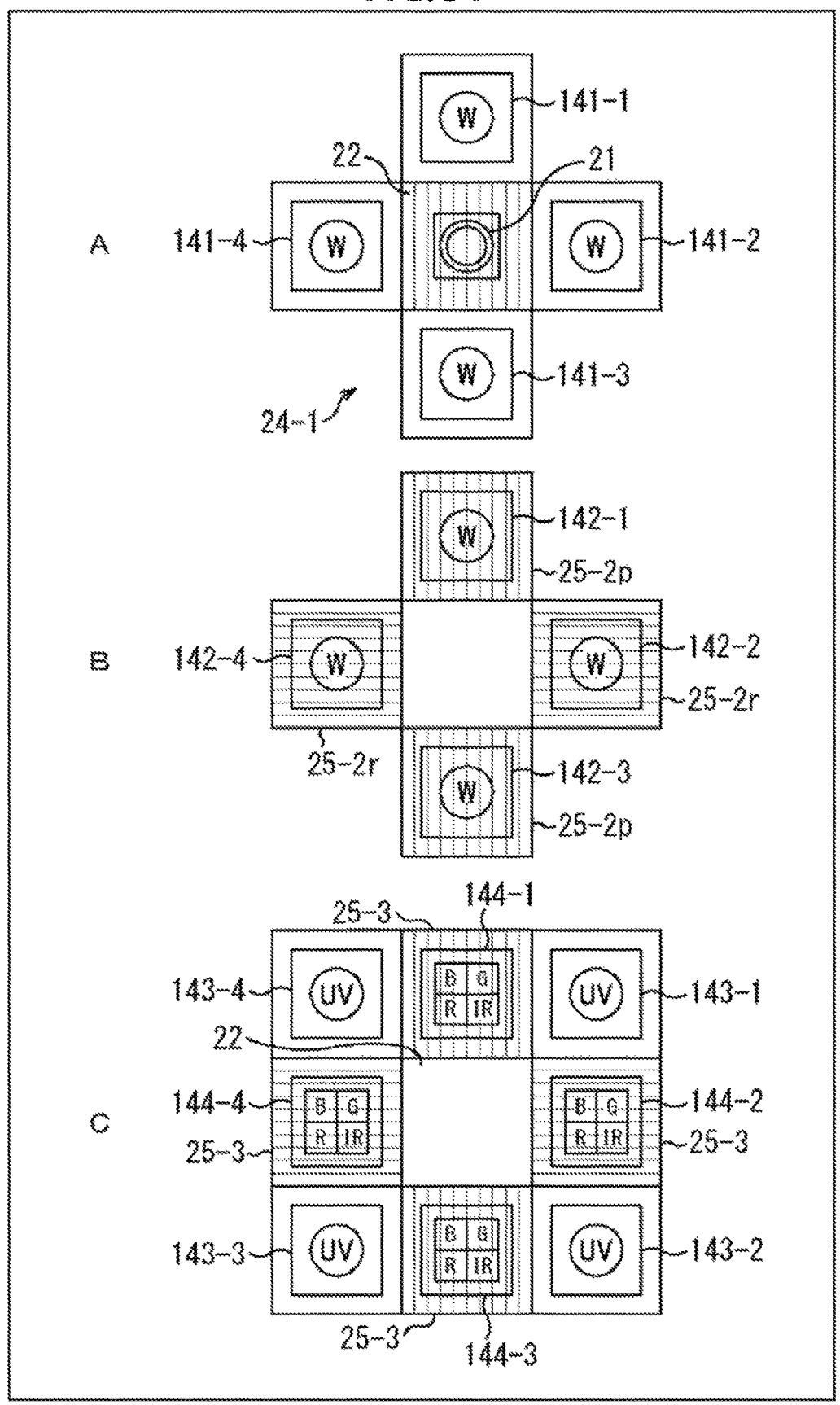
FIG. 31 illustrates a tenth arrangement example of light sources forming an illumination unit in FIG. 30.

FIG. 31 illustrates an arrangement example (hereinafter, referred to as "ninth arrangement example") of light sources forming the three-dimensional illumination units 24-1 to 24-3 in FIG. 30.

As illustrated in FIG. 31A, the illumination unit 24-1 arranged in the first layer includes four LEDs 141-1 to 141-4, and those LEDs are arranged at equal intervals around the optical axis of the camera 21 serving as a center. For each LED 141, an LED that generates W light is employed.

As illustrated in FIG. 31B, the illumination unit 24-2 arranged in the second layer includes four LEDs 142-1 to 142-4, and those LEDs are arranged at equal intervals around the optical axis of the camera 21 serving as a center. For each LED 142, an LED that generates W light is employed. The polarizers 25-2$p$ whose polarization direction is in parallel to that of the analyzer 22 arranged in front of the camera 21 are arranged in front of the LEDs 142-1 and 142-3. Polarizers 25-2$p$ whose polarization direction is orthogonal to that of the analyzer 22 arranged in front of the camera 21 are arranged in front of the LEDs 142-3 and 142-3.

As illustrated in FIG. 31C, the illumination unit 24-2 arranged in the third layer includes eight LEDs 143-1 to 143-4 and 144-1 to 144-4, and those LEDs are arranged at equal intervals around the optical axis of the camera 21 serving as a center. For each LED 143, an LED that generates UV light is employed. In each LED 144, one package including four chips that generate R, G, B, and IR light having different wavelengths, respectively, is employed. In each LED 144, each chip can be independently turned on and turned off. Polarizers 25-3$p$ whose polarization direction is in parallel to that of the analyzer 22 arranged in front of the camera 21 are arranged in front of the LEDs 144-1 and 144-3. Polarizers 25-3$r$ whose polarization direction is orthogonal to that of the analyzer 22 arranged in front of the camera 21 are arranged in front of the LEDs 144-2 and 144-4.

Note that the illumination units 24-1 to 24-3 can be rotated around the optical axis of the camera 21, and the illumination unit 24-2 in the second layer is arranged at a position where light emitted therefrom is not blocked by the illumination unit 24-3 in the third layer. Similarly, the illumination unit 24-1 in the first layer is arranged at a position where light emitted therefrom is not blocked by the illumination unit 24-2 in the second layer or the illumination unit 24-3 in the third layer.

Note that, in the case of the tenth arrangement example, a large number of LEDs are arranged in the third layer that is the closest to the skin observation area, but the large number of LEDs may be arranged in the first layer or the second layer. Configurations of chips forming an LED and one package are not limited to the examples illustrated in FIG. 31 but are arbitrary.

Correspondence between measurement items and ON of the light sources in the tenth arrangement example is similar to the correspondence between the measurement items and ON of the light sources in the eighth arrangement example described with reference to FIG. 24, and therefore description thereof is omitted.

Tenth Example Configuration of Image Acquisition Unit 13

Figure 32:
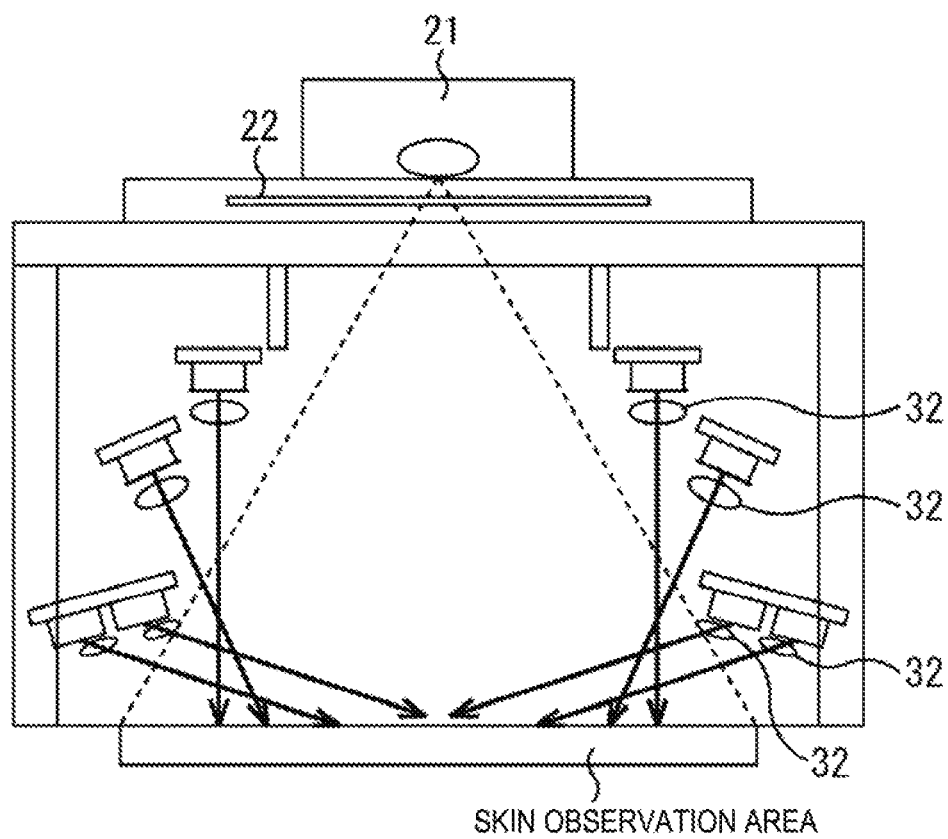
FIG. 32 is a cross-sectional view illustrating a tenth example configuration of an image acquisition unit in FIG. 4.

FIG. 32 illustrates a cross-section of a tenth example configuration of the image acquisition unit 13. The tenth example configuration is configured such that the lenses 32 serving as light guide members are arranged in front of the respective illumination units 24-1 to 24-3 in the ninth example configuration illustrated in FIG. 30. Note that constituent elements common to the ninth example configuration are denoted by the same numbers, and therefore description thereof is omitted.

Regarding an arrangement example of the light sources forming the illumination units 24-1 to 24-3, not only the tenth arrangement example illustrated in FIG. 31 but also arbitrary arrangement can be employed.

The lenses 32 are curved in a travelling direction of irradiation light emitted by the illumination units 24-1 to 24-3 to irradiate the skin observation area. Because the lenses 32 are arranged, it is possible to efficiently irradiate the skin observation area with irradiation light emitted from the illumination units 24-1 to 24-3.

Note that central axes of (light sources included in) the illumination units 24-1 to 24-3 and central axes of the lenses 32 corresponding thereto do not necessarily correspond to each other. Instead, irradiation light can be emitted more efficiently in some cases by decentering both the central axes.

Arbitrary light guide members such as light pipes may be arranged instead of the lenses 32.

Computer (or Program) to which Present Disclosure is Applied

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Figure 33:
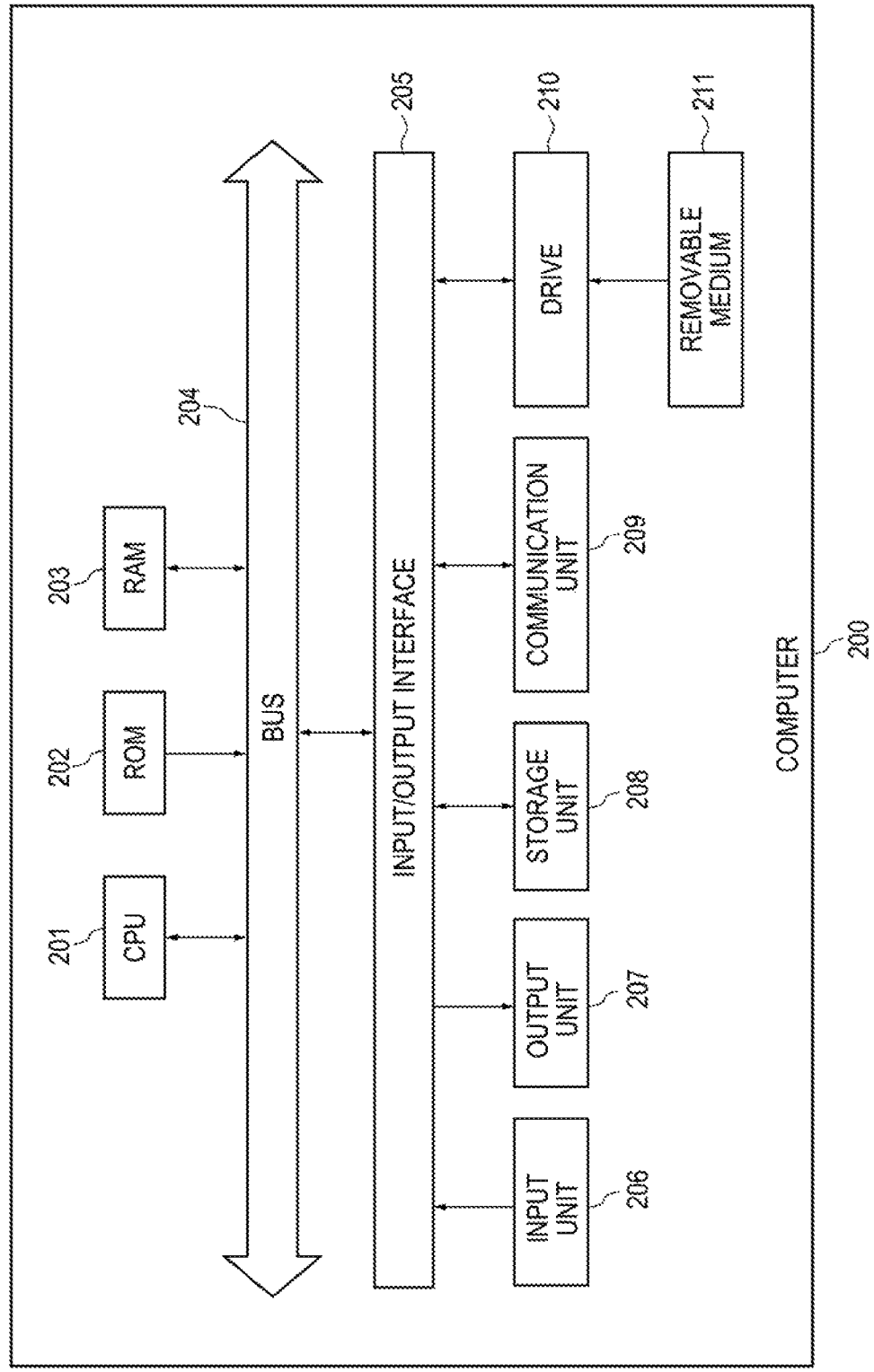
FIG. 33 is a block diagram showing an example configuration of a computer to which the present disclosure is applied.

FIG. 33 is a block diagram showing an example configuration of the hardware of a computer that executes the series of processes described earlier according to a program.

In a computer 200, a CPU (Central Processing Unit) 201, a ROM (Read Only Memory) 202, and a RAM (Random Access Memory) 203 are mutually connected by a bus 204.

An input/output interface 205 is also connected to the bus 204. An input unit 206, an output unit 207, a storage unit 208, a communication unit 209, and a drive 210 are connected to the input/output interface 205.

The input unit 206 is configured from a keyboard, a mouse, a microphone or the like. The output unit 207 configured from a display, a speaker or the like. The storage unit 208 is configured from a hard disk, a non-volatile memory or the like. The communication unit 209 is configured from a network interface or the like. The drive 210 drives a removable medium 211 such as a magnetic disk, an optical disk, a magneto-optical disk, a semiconductor memory or the like.

In the computer 200 configured as described above, as one example the CPU 201 loads a program stored in the storage unit 208 via the input/output interface 205 and the bus 204 into the RAM 203 and executes the program to carry out the series of processes described earlier.

As one example, the program executed by the computer 200 (the CPU 201) may be provided by being recorded on the removable medium 211 as a packaged medium or the like. The program can also be provided via a wired or wireless transfer medium, such as a local area network, the Internet, or a digital satellite broadcast.

In the computer 200, by loading the removable medium 211 into the drive 210, the program can be installed into the storage unit 208 via the input/output interface 205. It is also possible to receive the program from a wired or wireless transfer medium using the communication unit 209 and install the program into the storage unit 208. As another alternative, the program can be installed in advance into the ROM 202 or the storage unit 208.

Note that the program executed by the computer 200 may be a program in which processes are carried out in a time series in the order described in this specification or may be a program in which processes are carried out in parallel or at necessary timing, such as when the processes are called.

An embodiment of the disclosure is not limited to the embodiments described above, and various changes and modifications may be made without departing from the scope of the disclosure.

Additionally, the present technology may also be configured as below.

(1) An image analysis device, including
an image acquisition unit including
an illumination unit including a light emitting unit in which a plurality of light emitting elements including at least a light emitting element configured to emit visible light and a light emitting element configured to emit invisible light are packaged, and
an image pickup unit configured to capture an image of reflection light generated by causing irradiation light emitted from the illumination unit to be reflected by an analysis target.

(2) The image analysis device according to (1),
wherein, in the light emitting unit, the plurality of light emitting elements including at least a light emitting element configured to emit red light that is visible light, a light emitting element configured to emit green light that is visible light, and a light emitting element configured to emit infrared radiation that is invisible light are packaged.

(3) The image analysis device according to (1) or (2),
wherein the image acquisition unit further includes
a polarizer arranged in an optical path of the irradiation light emitted from the illumination unit, and
an analyzer arranged in an optical path in which the reflection light is incident on the image pickup unit.

(4) The image analysis device according to any of (1) to (3),
wherein the image acquisition unit further includes
a light guide member configured to guide the irradiation light emitted from the irradiation unit to the analysis target.

(5) The image analysis device according to (4),
wherein the light guide member has an arbitrary optical surface shape.

(6) The image analysis device according to any of (1) to (5),
wherein the illumination unit includes the plurality of light emitting units, and
wherein the plurality of light emitting units are arranged at equal intervals around an optical axis of the image pickup unit.

(7) The image analysis device according to (6),
wherein the plurality of light emitting units forming the illumination unit are planarly arranged at equal intervals around the optical axis of the image pickup unit.

(8) The image analysis device according to (6),
wherein the plurality of light emitting units forming the illumination unit are three-dimensionally arranged at equal intervals around the optical axis of the image pickup unit so as to form a multilayer.

(9) The image analysis device according to any of (6) to (8),
wherein the plurality of light emitting units forming the illumination unit are arranged at different angles so as to face the analysis target.

(10) The image analysis device according to any of (1) to (9),
wherein the illumination unit changes a wavelength of the irradiation light by changing the light emitting element to emit light in accordance with an analysis item.

(11) The image analysis device according to (10), further including
an operation input unit to which user operation for selecting the analysis item is input.

(12) The image analysis device according to any of (1) to (11), further including
an image analysis unit configured to analyze an image captured by the image pickup unit.

(13) An image analysis method using an image analysis device that includes an image acquisition unit including
an illumination unit including a light emitting unit in which a plurality of light emitting elements including at least a light emitting element configured to emit visible light and a light emitting element configured to emit invisible light are packaged, and
an image pickup unit configured to capture an image of reflection light generated by causing irradiation light emitted from the illumination unit to be reflected by an analysis target, the method including:
an irradiation step of emitting irradiation light by using the illumination unit; and
an image capturing step of capturing, by using the image pickup unit, an image of reflection light generated by causing the irradiation light emitted from the illumination unit to be reflected by the analysis target.

(14) A program for controlling an image analysis device that includes an image acquisition unit including
an illumination unit including a light emitting unit in which a plurality of light emitting elements including at least a light emitting element configured to emit visible light and a light emitting element configured to emit invisible light are packaged, and
image pickup unit configured to capture an image of reflection light generated by causing irradiation light emitted from the illumination unit to be reflected by an analysis target,
the program causing a computer of the image analysis device to execute processing including
an illumination step of controlling the illumination unit in a manner that the illumination unit emits irradiation light, and
an image capturing step of controlling the image pickup unit in a manner that the image pickup unit captures an image of reflection light generated by causing the irradiation light emitted from the illumination unit to be reflected by the analysis target.

(15) An illumination device, including
a plurality of light emitting units in which a plurality of light emitting elements including at least a light emitting element configured to emit visible light and a light emitting element configured to emit invisible light are packaged.

REFERENCE SIGNS LIST 10 image analysis device
11 operation input unit
12 control unit
13 image acquisition unit
14 image analysis unit
15 display unit
21 camera
22 analyzer
23 PCB
24 illumination unit
25 polarizer
31 light guide member
32 lens
33 light pipe 61, 71, 72, 81, 82, 91, 101, 102, 111 to 114, 121 to 123, 131 to 133, 141 to 143 LED
200 computer
201 CPU

The invention claimed is:

1. An image analysis device, comprising:
an image acquisition unit that includes:
an illumination unit including a light emitting unit, wherein
the illumination unit is directed towards an inner surface of a housing of the image acquisition unit,
the light emitting unit includes a plurality of light emitting elements,
the plurality of light emitting elements includes at least a light emitting element configured to emit visible light and a light emitting element configured to emit invisible light,
the illumination unit is configured to:
emit irradiation light towards the inner surface of the housing; and
change a wavelength of the irradiation light based on an analysis item associated with an analysis target, wherein
the analysis target corresponds to human skin,
the analysis item corresponds to a state of the human skin, and
the wavelength is changed based on a change in light emitting element from a first light emitting element of the plurality of light emitting elements to a second light emitting element of the plurality of light emitting elements;
a light pipe configured to guide the irradiation light, emitted from the illumination unit, to the analysis target to generate reflection light; and
a camera configured to capture an image of the reflection light.

2. The image analysis device according to claim 1, wherein the plurality of light emitting elements further includes at least:
a light emitting element configured to emit red light that is the visible light,
a light emitting element configured to emit green light that is the visible light, and
a light emitting element configured to emit infrared radiation that is the invisible light.

3. The image analysis device according to claim 2, wherein the image acquisition unit further includes:
a polarizer in a first optical path of the irradiation light emitted from the illumination unit; and
an analyzer in a second optical path in which the reflection light is incident on the camera.

4. The image analysis device according to claim 2, wherein
the illumination unit includes a plurality of light emitting units, and
the plurality of light emitting units are at equal intervals around an optical axis of the camera.

5. The image analysis device according to claim 4, wherein
the plurality of light emitting units of the illumination unit are in a planar arrangement.

6. The image analysis device according to claim 4, wherein
the plurality of light emitting units of the illumination unit are in a three-dimensional arrangement, and
the plurality of light emitting units are at the equal intervals around the optical axis of the camera so as to form a multilayer.

7. The image analysis device according to claim 2, further comprising a Central Processing unit (CPU) configured to analyze the image captured by the camera.

8. The image analysis device according to claim 1, wherein the light pipe has an arbitrary optical surface shape.

9. The image analysis device according to claim 1, further comprising an input/output interface configured to select the analysis item based on a user input.

10. The image analysis device according to claim 1, wherein the analysis item is one of a melanin index of the human skin, or an erythema index of the human skin.

11. An image analysis method, comprising:
in an image analysis device that includes an image acquisition unit, wherein
the image acquisition unit includes:
a camera;
an illumination unit including a light emitting unit; and
a light pipe configured to guide irradiation light, emitted from the illumination unit, to an analysis target to generate reflection light,
the illumination unit is directed towards an inner surface of a housing of the image acquisition unit,
the light emitting unit includes a plurality of light emitting elements, and
the plurality of light emitting elements includes at least a light emitting element configured to emit visible light and a light emitting element configured to emit invisible light, the method comprising:
emitting, by the illumination unit, the irradiation light towards the inner surface of the housing;
changing, by the illumination unit, a wavelength of the irradiation light based on an analysis item associated with the analysis target, wherein
the analysis target corresponds to human skin,
the analysis item corresponds to a state of the human skin, and
the wavelength is changed based on a change in light emitting element from a first light emitting element of the plurality of light emitting elements to a second light emitting element of the plurality of light emitting elements; and
capturing, by the camera, an image of the reflection light.

12. A non-transitory computer-readable medium having stored thereon, computer-executable instructions which, when executed by an image analysis device that includes an image acquisition unit, wherein
the image acquisition unit includes:
a camera;
an illumination unit including a light emitting unit; and
a light pipe configured to guide irradiation light, emitted from the illumination unit, to an analysis target to generate reflection light,
the illumination unit is directed towards an inner surface of a housing of the image acquisition unit,
the light emitting unit includes a plurality of light emitting elements,
the plurality of light emitting elements includes at least a light emitting element configured to emit visible light and a light emitting element configured to emit invisible light,
cause the image analysis device to execute operations, the operations comprising:

controlling the illumination unit such that the illumination unit emits irradiation light towards the inner surface of the housing;

controlling the illumination unit to change a wavelength of the irradiation light based on an analysis item associated with the analysis target, wherein
the analysis target corresponds to human skin,
the analysis item corresponds to a state of the human skin, and
the wavelength is changed based on a change in light emitting element from a first light emitting element of the plurality of light emitting elements to a second light emitting element of the plurality of light emitting elements; and controlling the camera such that the camera captures an image of the reflection light.

13. An illumination device, comprising:

a plurality of light emitting units in which a plurality of light emitting elements includes at least a light emitting element configured to emit visible light and a light emitting element configured to emit invisible light, wherein the illumination device is directed towards an inner surface of a housing of an image acquisition unit, irradiation light emitted from the illumination device, is guided by a light pipe, to an analysis target to generate reflection light, the illumination device is configured to:
emit the irradiation light towards the inner surface of the housing; and
change a wavelength of the irradiation light based on an analysis item associated with the analysis target, wherein the analysis target corresponds to human skin, the analysis item corresponds to a state of the human skin, and the wavelength is changed based on a change in light emitting element from a first light emitting element of the plurality of light emitting elements to a second light emitting element of the plurality of light emitting elements.

\* \* \* \* \*